(12) United States Patent
Egusa

(10) Patent No.: US 9,974,884 B2
(45) Date of Patent: May 22, 2018

(54) BONE REGENERATION AGENT

(71) Applicant: OSAKA UNIVERSITY, Osaka (JP)

(72) Inventor: Hiroshi Egusa, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 74 days.

(21) Appl. No.: 15/032,082

(22) PCT Filed: Oct. 30, 2014

(86) PCT No.: PCT/JP2014/078934
§ 371 (c)(1),
(2) Date: Jun. 21, 2016

(87) PCT Pub. No.: WO2015/064705
PCT Pub. Date: May 7, 2015

(65) Prior Publication Data
US 2016/0287753 A1 Oct. 6, 2016

(30) Foreign Application Priority Data
Oct. 31, 2013 (JP) ................................ 2013-227176

(51) Int. Cl.
| C12N 5/00 | (2006.01) |
| A61L 27/36 | (2006.01) |
| A61K 35/32 | (2015.01) |
| C12N 5/074 | (2010.01) |
| A61L 27/54 | (2006.01) |
| A61K 38/39 | (2006.01) |
| A61K 33/06 | (2006.01) |
| A61K 35/28 | (2015.01) |
| A61K 35/545 | (2015.01) |
| A61L 27/12 | (2006.01) |
| A61L 27/24 | (2006.01) |
| C12N 5/077 | (2010.01) |
| A61L 27/38 | (2006.01) |

(52) U.S. Cl.
CPC .......... *A61L 27/3683* (2013.01); *A61K 33/06* (2013.01); *A61K 35/28* (2013.01); *A61K 35/32* (2013.01); *A61K 35/545* (2013.01); *A61K 38/39* (2013.01); *A61L 27/12* (2013.01); *A61L 27/24* (2013.01); *A61L 27/365* (2013.01); *A61L 27/3633* (2013.01); *A61L 27/3691* (2013.01); *A61L 27/3834* (2013.01); *A61L 27/54* (2013.01); *C12N 5/0654* (2013.01); *C12N 5/0696* (2013.01); *A61L 2300/412* (2013.01); *A61L 2300/64* (2013.01); *A61L 2400/06* (2013.01); *A61L 2430/02* (2013.01); *C12N 2500/14* (2013.01); *C12N 2506/45* (2013.01); *C12N 2533/54* (2013.01)

(58) Field of Classification Search
CPC .................. A61K 27/3638; A61K 27/3834
See application file for complete search history.

(56) References Cited

U.S. PATENT DOCUMENTS
2003/0060892 A1 3/2003 Richter et al.

FOREIGN PATENT DOCUMENTS
| JP | 8-229114 | 9/1996 |
| JP | 2000-262609 | 9/2000 |
| JP | 2004-518466 | 6/2004 |
| JP | 2004-305259 | 11/2004 |
| JP | 2010-75247 | 4/2010 |
| JP | 2011-41472 | 3/2011 |
| JP | 2011-239815 | 12/2011 |
| JP | 2012-16517 | 1/2012 |

OTHER PUBLICATIONS

International Search Report dated Feb. 3, 2015 in International Application No. PCT/JP2014/078934.
International Preliminary Report on Patentability dated May 6, 2016 in International Application No. PCT/JP2014/078934.
Soo-Hyun Kim, et al., "Extracellular matrix and cell signalling: the dynamic cooperation of integrin, proteoglycan and growth factor receptor", Journal of Endocrinology, vol. 209, pp. 139-151, 2011.
Yizhi Meng, et al., "Biomineralization of a Self-Assembled Extracellular Matrix for Bone Tissue Engineering", Tissue Engineering Part A, vol. 15, No. 2, pp. 355-366, 2009.
Hiroshi Egusa, et al., "Stem cells in dentistry—Part II: Clinical applications", Journal of Prosthodontic Research, vol. 56, pp. 229-248, 2012.
Junichi Sasaki, et al., "Development of endochondral ossification analysis tool using 3D cell constructs", Journal of Japanese Society for Dental Materials and Devices, vol. 31, No. 2, pp. 138, 2012 (with partial English translation).
Hiroki Kayashima, et al., "Development of iPS cell technology-based treatment for bone augmentation", Journal of Japanese Society of Oral Implantology, vol. 26, Special issue, pp. 334, P-2-9, 2013 (with partial English translation).

(Continued)

*Primary Examiner* — Marcia S Noble
(74) *Attorney, Agent, or Firm* — Wenderoth, Lind & Ponack, L.L.P.

(57) ABSTRACT

Provided is a bone regeneration agent comprising an inactivated cell construct derived from stem cells as a source material, the inactivated cell construct at least containing a mineral and an extracellular matrix. The bone regeneration agent has osteoconductive and osteoinductive abilities, and is inexpensively producible and size-controllable. Also provided is a method comprising the steps of:
(1) inducing differentiation of stem cells into mineral-producing cells in agitated culture under the condition of 0.01 to 1.00 Hz to give a cell aggregate at least containing a mineral and an extracellular matrix, or
(1') inducing differentiation of stem cells genetically engineered to overexpress a protein associated with bone formation into mineral-producing cells in agitated or static culture, to give a cell aggregate at least containing a mineral and an extracellular matrix, and
(2) inactivating the cell aggregate obtained in the preceding step. The method enables easy production of the above-mentioned bone regeneration agent.

6 Claims, 8 Drawing Sheets

(56) References Cited

OTHER PUBLICATIONS

Hiroki Kayashima, et al., "Enhanced osteogenesis of gingival fibroblast-derived iPS cells by small molecules", Journal of Japanese Society of Oral Implantology, vol. 24, Special issue, pp. 142, T-6-4, 2011 (with partial English Translation).
Sujata Kale, et al., "Three-dimensional cellular development is essential for ex vivo formation of human bone", Nature Biotechnology, vol. 18, pp. 954, 2000.
Jun-Ichi Sasaki, et al., "In vitro reproduction of endochondral ossification using a 3D mesenchymal stem cell construct", Integrative Biology, pp. 1207-1210, 2012.
Hiroshi Egusa, et al., "Comparative Analysis of Mouse-Induced Pluripotent Stem Cells and Mesenchymal Stem Cells During Osteogenic Differentiation In Vitro", Stem Cells and Development, vol. 23, No. 18, pp. 2156, 2014.
Mizuho Kittaka, et al., "Clumps of a mesenchymal stromal cell/extracellular matrix complex can be a novel tissue engineering therapy for bone regeneration", Cytotherapy, pp. 1-12, 2015.

BONE REGENERATION AGENT

TECHNICAL FIELD

The present invention relates to a bone regeneration agent for use in the surgical treatment of injured hard bone tissues.

BACKGROUND ART

When bone tissue is broken or otherwise damaged, bone-forming cells, called osteoblasts, proliferate and differentiate to regenerate bone. In the case of mild damage, fixation of the affected area helps osteoblasts function, leading to bone healing. In the case of compound fracture, intra-articular injury, concomitant osteomyelitis, etc., osteoblasts cannot effectively function and various surgical interventions, such as autologous bone grafting, implantation of artificial joints and artificial bones and injection of bone substitute materials, are applied. Recently, with the progress of aging, there is a growing demand for artificial bones and bone substitute materials which replace bone lost due to bone tumor excision, comminuted fracture, bone defect associated with arthrodesis in rheumatoid arthritis, alveolar ridge resorption, etc.

Currently, most of clinically-used artificial bones and bone substitute materials are composed of calcium phosphate, which is a bioactive, biocompatible and osteoconductive substance. Known calcium phosphate-based bone substitute materials include non-absorptive materials such as hydroxyapatite ($Ca_{10}(PO_4)_6(OH)_2$) (Patent Literature 1 and 2) and absorptive materials such as β-tricalcium phosphate (β-TCP) (Patent Literature 3, 4, 5 and 6).

However, these biomaterials are inferior to autologous bones in osteoinductive activity etc. In addition, non-absorptive materials are not replaced with natural bone, thus causing problems in terms of bone strength and implant-bone integration (osseointegration) during and/or after healing. Absorptive materials are reduced in volume during the replacement with natural bone, thus causing problems in terms of bone morphology after healing. Therefore, the use of these materials in surgical intervention does not always lead to good prognosis.

Under such circumstances, there is a demand to promote the development of next-generation artificial bones and bone substitute materials which are a hybrid type of product having a combination of an artificial bone structure and a growth factor protein such as BMP (bone morphogenetic protein).

Meanwhile, "extracellular matrix", which is a fibrous and net-like structure outside somatic cells, has been shown to be important for bone tissue regeneration (Non Patent Literature 1 and 2). In this view, a simple mixture of a calcium phosphate material with a growth factor can hardly provide satisfactory results in bone regeneration. Particularly in dentistry, the improvement of the outcome of implant treatment requires technologies for regenerating a vertical bone defect resulting from tooth loss, but vertical bone regeneration has not been achieved with the use of conventional bone substitute materials.

On the other hand, stem cell-based approaches in bone regenerative medicine are regarded as more effective than conventional bone regeneration technologies because the cells themselves produce extracellular matrices and growth factors (Non Patent Literature 3). Particularly, induced pluripotent stem cells (iPS cells), which were first established in Japan, are a type of stem cells that can be generated from patient's own cells without the destruction of fertilized eggs, which is essential for generating embryonic stem cells (ES cells), and thus are expected to be clinically applied. However, the biggest problem of the iPS cell-based treatment is the risk of neoplastic transformation of transplanted cells due to the use of living stem cells. Another problem is the need of large-scale equipment and facilities for cell culture.

Therefore, the development of novel stem cell-based therapies in bone regenerative medicine which are safe and highly therapeutically effective has been desired.

CITATION LIST

Patent Literature

Patent Literature 1: JP-A 8-229114
Patent Literature 2: JP-W 2004-518466
Patent Literature 3: JP-A 2000-262609
Patent Literature 4: JP-A 2010-75247
Patent Literature 5: JP-A 2011-239815
Patent Literature 6: JP-A 2012-16517

Non Patent Literature

Non Patent Literature 1:
Kim S H, Turnbull J, Guimond S, Journal of Endocrinology, 2011 May; 209 (2): 139-151.
Non Patent Literature 2:
TISSUE ENGINEERING: Part A. February 2009, 15 (2): 355-366.
Non Patent Literature 3:
Egusa H, Sonoyama W, Nishimura M, Atsuta I, Akiyama K, Journal of Prosthodontic Research, 2012 October; 56 (4): 229-48.

SUMMARY OF INVENTION

Technical Problem

The present invention is intended to provide a bone regeneration agent which is safe and has osteoconductive and osteoinductive abilities. In addition, the present invention is intended to provide a simple method for producing the bone regeneration agent. Furthermore, the present invention is intended to provide an inexpensively producible, size-controllable bone regeneration agent.

Solution to Problem

The present inventor conducted extensive research to achieve the above-mentioned objects, and as a result, found that a bone regeneration agent which is safe and has osteoconductive and osteoinductive abilities can be provided by inducing the differentiation of stem cells and subsequently inactivating the differentiated cells. Based on this finding, the present inventor conducted further research and completed the present invention.

That is, the present invention relates to the following.
[1] A bone regeneration agent comprising an inactivated cell construct derived from stem cells as a source material, the inactivated cell construct at least containing a mineral and an extracellular matrix.
[2] The bone regeneration agent according to the above [1], wherein the inactivated cell construct is prepared by inactivating a cell aggregate at least containing a mineral and an extracellular matrix.
[3] The bone regeneration agent according to the above [2], wherein the cell aggregate at least containing a mineral and an extracellular matrix is obtained by inducing differentiation of the stem cells into mineral-producing cells.

[4] The bone regeneration agent according to the above [3], wherein the stem cell is an adult stem cell or a stem cell having pluripotency, namely a pluripotent stem cell.

[5] The bone regeneration agent according to the above [4], wherein the pluripotent stem cell is one or more types selected from the group consisting of an ES cell, an EG cell and an iPS cell.

[6] The bone regeneration agent according to any one of the above [1] to [5], wherein the extracellular matrix is mainly composed of a collagen protein.

[7] The bone regeneration agent according to any one of the above [1] to [6], wherein the inactivated cell construct has a peak for a phosphate at around $1000\pm200$ cm$^{-1}$, a peak for amide II at around $1550\pm100$ cm$^{-1}$ and a peak for amide I at around $1650\pm100$ cm$^{-1}$ in its measured FT-IR (KBr) spectrum.

[8] A method for producing the bone regeneration agent according to any one of the above [1] to [7], the method comprising the steps of:
(1) inducing differentiation of stem cells into mineral-producing cells in agitated culture under the condition of 0.01 to 1.00 Hz to give a cell aggregate at least containing a mineral and an extracellular matrix, or
(1') inducing differentiation of stem cells genetically engineered to overexpress a protein associated with bone formation into mineral-producing cells in agitated or static culture, to give a cell aggregate at least containing a mineral and an extracellular matrix, and
(2) inactivating the cell aggregate obtained in the preceding step.

[9] The method according to the above [8], the method comprising the steps of:
(1) inducing differentiation of stem cells into mineral-producing cells in agitated culture under the condition of 0.01 to 1.00 Hz to give a cell aggregate at least containing a mineral and an extracellular matrix, and
(2) inactivating the cell aggregate obtained in the preceding step.

[10] The method according to the above [8] or [9], wherein the stem cell is an adult stem cell or a stem cell having pluripotency, namely a pluripotent stem cell.

[11] The method according to the above [10], wherein the pluripotent stem cell is one or more types selected from the group consisting of an ES cell, an EG cell and an iPS cell.

[12] The method according to any one of the above [8] to [11], wherein the inactivation is performed by lyophilization.

[13] The method according to any one of the above [8] to [12], wherein the extracellular matrix is mainly composed of a collagen protein.

[14] The method according to any one of the above [8] to [13], wherein the agitated culture in step (1) is performed in the presence of an osteoblastic differentiation-inducing factor.

[15] The method according to the above [14], wherein the osteoblastic differentiation-inducing factor is one or more kinds selected from the group consisting of dexamethasone, β-glycerophosphoric acid and ascorbic acid 2-phosphate.

[16] The method according to any one of the above [8] to [15], wherein the period of the agitated culture is 5 days or more.

[17] A method for tissue regeneration, comprising a step of administering, to a human or a non-human mammal in need of tissue regeneration, a bone regeneration agent obtained by a method comprising the steps of:

(1) inducing differentiation of stem cells into mineral-producing cells in agitated culture under the condition of 0.01 to 1.00 Hz to give a cell aggregate at least containing a mineral and an extracellular matrix, or
(1') inducing differentiation of stem cells genetically engineered to overexpress a protein associated with bone formation into mineral-producing cells in agitated or static culture, to give a cell aggregate at least containing a mineral and an extracellular matrix, and
(2) inactivating the cell aggregate obtained in the preceding step.

[18] A method for tissue regeneration, comprising a step of administering, to a human or a non-human mammal in need of tissue regeneration, a bone regeneration agent comprising an inactivated cell construct derived from stem cells as a source material, the inactivated cell construct at least containing a mineral and an extracellular matrix.

[19] Use of a composition for production of a bone regeneration agent, the composition being obtainable by a method comprising the steps of:
(1) inducing differentiation of stem cells into mineral-producing cells in agitated culture under the condition of 0.01 to 1.00 Hz to give a cell aggregate at least containing a mineral and an extracellular matrix, or
(1') inducing differentiation of stem cells genetically engineered to overexpress a protein associated with bone formation into mineral-producing cells in agitated or static culture, to give a cell aggregate at least containing a mineral and an extracellular matrix, and
(2) inactivating the cell aggregate obtained in the preceding step.

[20] Use of a composition for production of a bone regeneration agent, the composition comprising an inactivated cell construct derived from stem cells as a source material, the inactivated cell construct at least containing a mineral and an extracellular matrix.

[21] A composition used for bone regeneration, the composition being obtainable by a method comprising the steps of:
(1) inducing differentiation of stem cells into mineral-producing cells in agitated culture under the condition of 0.01 to 1.00 Hz to give a cell aggregate at least containing a mineral and an extracellular matrix, or
(1') inducing differentiation of stem cells genetically engineered to overexpress a protein associated with bone formation into mineral-producing cells in agitated or static culture, to give a cell aggregate at least containing a mineral and an extracellular matrix, and
(2) inactivating the cell aggregate obtained in the preceding step.

[22] A composition used for bone regeneration, the composition comprising an inactivated cell construct derived from stem cells as a source material, the inactivated cell construct at least containing a mineral and an extracellular matrix.

Advantageous Effects of Invention

The bone regeneration agent of the present invention is free from the risk of neoplastic transformation, is safe, and has osteoconductive ability (the ability to integrate with bone) and osteoinductive ability (the ability to form bone). Furthermore, the bone regeneration agent of the present invention is appropriately replaced with natural bone without the reduction in vertical volume, thus enabling favorable osseointegration. In addition, the production method of the present invention enables easy production of a bone regeneration agent. The bone regeneration agent of the present invention is inexpensively producible, size-controllable and easy in handling at the time of injection.

DESCRIPTION OF EMBODIMENTS

Figure 1:
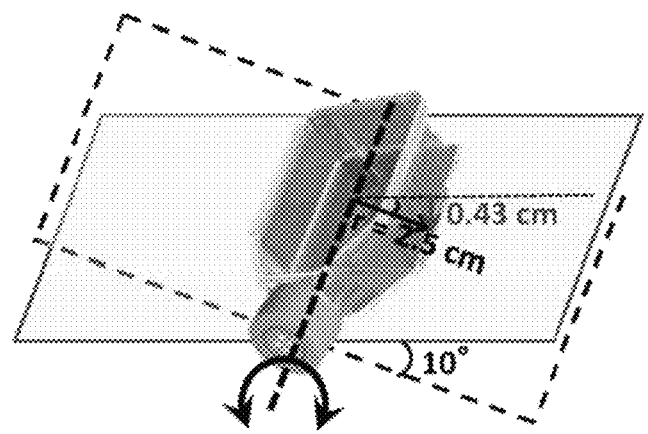
FIG. 1 shows an embodiment of the bioreactor used in agitated culture in the present invention.

The bone regeneration agent of the present invention comprises an inactivated cell construct derived from stem cells as a source material, the inactivated cell construct at least containing a mineral and an extracellular matrix. In the present invention, the bone regeneration agent has osteoconductive ability (the ability to integrate with bone) and osteoinductive ability (the ability to form bone) and is also called a bone substitute material.

The type of the stem cell used in the bone regeneration agent of the present invention is not particularly limited, and the examples include an adult stem cell and a stem cell having pluripotency, namely a pluripotent stem cell. The type of the adult stem cell is not particularly limited, and the examples include a mesenchymal stem cell, a hematopoietic stem cell and a neural stem cell. The type of the pluripotent stem cell, namely a stem cell having pluripotency, is not particularly limited, and the examples include an iPS cell (induced pluripotent stem cell), an EG cell (embryonic germ cell) and an ES cell (embryonic stem cell). Preferred is an iPS cell because this type of cell can be generated without the destruction of fertilized eggs. The stem cell used in the present invention may be derived from any mammal from which an adult stem cell is available or a pluripotent stem cell has been established or can be established. Examples of the mammal include a human, a mouse, a rat, a monkey, a dog, a pig, cattle, a cat, a goat, a sheep, a rabbit, a guinea pig and a hamster. Preferred are a human, a mouse, a rat, a monkey, a dog, etc., and more preferred are a human and a mouse.

The pluripotent stem cell can be obtained by a method which is known per se and appropriate for the type of the cell. For example, ES cells can be generated by culturing the inner cell mass of a mammalian blastocyst-stage embryo (see, for example, Manipulating the Mouse Embryo A Laboratory Manual, Second Edition, Cold Spring Harbor Laboratory Press (1994)), or by culturing an early embryo created by somatic nuclear transplantation (Wilmut et al., Nature, 385, 810 (1997); Cibelli et al., Science, 280, 1256 (1998); Akira Iritani et al., Protein, Nucleic Acid and Enzyme, 44, 892 (1999); Baguisi et al., Nature Biotechnology, 17, 456 (1999); Wakayama et al., Nature, 394, 369 (1998); Wakayama et al., Nature Genetics, 22, 127 (1999); Wakayama et al., Proc. Natl. Acad. Sci. USA, 96, 14984 (1999); and Rideout III et al., Nature Genetics, 24, 109 (2000); etc.), but the method for ES cell generation is not limited thereto.

iPS cells can be generated by introducing a nuclear reprogramming substance into somatic cells.

The somatic cell used as a source material for the generation of iPS cells may be any type of mammalian (for example, mouse or human) cells except germ cells. Examples of the somatic cell include oral mucosal cells (e.g., gingival fibroblasts, buccal mucosal fibroblasts, gingival epithelial cells, buccal mucosal epithelial cells, etc.), keratinized epithelial cells (e.g., keratinized epidermal cells etc.), mucosal epithelial cells (e.g., epithelial cells in the lingual epithelium etc.), exocrine gland epithelial cells (e.g., mammary gland cells etc.), hormone-secreting cells (e.g., adrenomedullary cells etc.), metabolizing or storage cells (e.g., hepatocytes etc.), luminal epithelial cells constituting boundary surfaces (e.g., type I alveolar cells etc.), luminal epithelial cells in the closed circulatory system (e.g., vascular endothelial cells etc.), cells with motile cilia (e.g., airway epithelial cells etc.), extracellular matrix-secreting cells (e.g., fibroblasts etc.), contractile cells (e.g., smooth muscle cells etc.), hematopoietic or immune cells (e.g., T lymphocytes etc.), sensory cells (e.g., rod cells etc.), autonomic neurons (e.g., cholinergic neurons etc.), supporting cells for sensory organs and peripheral neurons (e.g., satellite cells etc.), neuronal cells and glial cells in the central nervous system (e.g., astroglial cells etc.), pigment cells (e.g., retinal pigment epithelial cells etc.) and progenitor cells of the foregoing cells (e.g., tissue progenitor cells etc.). The level of differentiation of the cells is not particularly limited, and both undifferentiated progenitor cells (including somatic stem cells) and terminally differentiated mature cells can be used as the somatic cells as a source material in the present invention. Here, examples of the undifferentiated progenitor cells include tissue stem cells (somatic stem cells), such as neural stem cells, hematopoietic stem cells, mesenchymal stem cells and dental pulp stem cells.

The "nuclear reprogramming substance" in the present invention may be any substance (or a set of substances) capable of inducing the generation of iPS cells from somatic cells. The examples of such a substance include protein factors, nucleic acids encoding the same (which may be present in vectors) and low molecular weight compounds. In the case where the nuclear reprogramming substance is a protein factor or a nucleic acid encoding the same, the combinations shown below are preferable examples (only the names of protein factors are given in the following).

(1) Oct3/4, Klf4, c-Myc
(2) Oct3/4, Klf4, c-Myc, Sox2 (Sox2 can be replaced with Sox1, Sox3, Sox15, Sox17 or Sox18; Klf4 can be replaced with Klf1, Klf2 or Klf5; and c-Myc can be replaced with T58A mutant (active form), N-Myc or L-Myc)

(3) Oct3/4, Klf4, c-Myc, Sox2, Fbx15, Nanog, Eras, ECAT15S-2, TclI, β-catenin (active S33Y mutant)
(4) Oct3/4, Klf4, c-Myc, Sox2, TERT, SV40 Large T antigen (hereinafter referred to as SV40 LT)
(5) Oct3/4, Klf4, c-Myc, Sox2, TERT, HPV16 E6
(6) Oct3/4, Klf4, c-Myc, Sox2, TERT, HPV16 E7
(7) Oct3/4, Klf4, c-Myc, Sox2, TERT, HPV6 E6, HPV16 E7
(8) Oct3/4, Klf4, c-Myc, Sox2, TERT, Bmi1 (regarding the above combinations, see WO 2007/069666 (regarding the replacement of Sox2 with Sox18 and the replacement of Klf4 with Klf1 or Klf5 in the combination in the above (2), see Nature Biotechnology, 26, 101-106 (2008)); regarding the combination of Oct3/4, Klf4, c-Myc and Sox2, see also Cell, 126, 663-676 (2006), Cell, 131, 861-872 (2007), etc.; regarding the combination of Oct3/4, Klf4 (or Klf5), c-Myc and Sox2, see also Nat. Cell Biol., 11, 197-203 (2009); and regarding the combination of Oct3/4, Klf4, c-Myc, Sox2, hTERT and SV40 LT, see also Nature, 451, 141-146 (2008))
(9) Oct3/4, Klf4, Sox2 (see Nature Biotechnology, 26, 101-106 (2008))
(10) Oct3/4, Sox2, Nanog, Lin28 (see Science, 318, 1917-1920 (2007))
(11) Oct3/4, Sox2, Nanog, Lin28, hTERT, SV40 LT (see Stem Cells, 26, 1998-2005 (2008))
(12) Oct3/4, Klf4, c-Myc, Sox2, Nanog, Lin28 (see Cell Research (2008) 600-603)
(13) Oct3/4, Klf4, c-Myc, Sox2, SV40 LT (see also Stem Cells, 26, 1998-2005 (2008))
(14) Oct3/4, Klf4 (see Nature 454: 646-650 (2008) and Cell Stem Cell, 2: 525-528 (2008))
(15) Oct3/4, c-Myc (see Nature 454: 646-650 (2008))
(16) Oct3/4, Sox2 (see Nature, 451, 141-146 (2008) and WO 2008/118820)
(17) Oct3/4, Sox2, Nanog (see WO 2008/118820)
(18) Oct3/4, Sox2, Lin28 (see WO 2008/118820)
(19) Oct3/4, Sox2, c-Myc, Esrrb (Esrrb can be replaced with Esrrg; see Nat. Cell Biol., 11, 197-203 (2009))
(20) Oct3/4, Sox2, Esrrb (see Nat. Cell Biol., 11, 197-203 (2009))
(21) Oct3/4, Klf4, L-Myc
(22) Oct3/4, Nanog
(23) Oct3/4
(24) Oct3/4, Klf4, c-Myc, Sox2, Nanog, Lin28, SV40 LT (see Science, 324: 797-801 (2009))
(25) Oct3/4, Klf4, Sox2, any member of the GLIS family (for example, GLIS1, GLIS2, GLIS3 or the like may be used, and GLIS1 (GLIS family zinc finger 1) is preferably used; see WO 2010/098419 and WO 2011/102531)
(26) Oct3/4, Klf4, Sox2, any member of the IRX family (for example, IRX1, IRX2, IRX3, IRX4, IRX5, IRX6 or the like may be used, and IRX6 (iroquois homeobox protein 6) is preferably used; see WO 2010/098419)
(27) Oct3/4, Klf4, Sox2, any member of the PTX family (for example, PITX1, PITX2, PITX3 or the like may be used, and PITX2 (paired-like homeodomain transcription factor 2) is preferably used; PITX2 is known to have three isoforms (isoforms a, b and c), any isoform may be used, and isoform b is particularly preferably used; see WO 2010/098419)
(28) Oct3/4, Klf4, Sox2, DMRTB1 (DMRT-like family B with proline-rich C-terminal 1; see WO 2010/098419)

In the above [1] to (28), Oct3/4 may be replaced with another member of the Oct family, for example, Oct1A, Oct6 or the like. Sox2 (or Sox1, Sox3, Sox15, Sox17, Sox1S) may be replaced with another member of the Sox family, for example, Sox7 or the like. Lin28 may be replaced with another member of the Lin family, for example, Lin28b or the like.

Further, combinations which are not exactly the same as any one of the above [1] to (28) but contain all the components in any one of the above [1] to (28) and some other substance can also be included in the "nuclear reprogramming substance" as used herein. Furthermore, when some of the components in any one of the above [1] to (28) are endogenously expressed in somatic cells at a sufficient level required for nuclear reprogramming, a combination of only the other components can also be included in the "nuclear reprogramming substance" as used herein.

Among all the above combinations, preferable examples of the nuclear reprogramming substance include at least one substance, preferably a set of two or more substances, and more preferably a set of three or more substances selected from Oct3/4, Sox2, Klf4, c-Myc, Nanog, Lin28 and SV40 LT.

The mouse and human cDNA sequence data of the above-mentioned nuclear reprogramming substances can be obtained with reference to the NCBI accession numbers described in WO 2007/069666 or WO 2010/098419 (Nanog is described as "ECAT4" in these documents, and the mouse and human cDNA sequence data of Lin28, Lin28b, Esrrb, Esrrg and L-Myc can be obtained with reference to the NCBI accession numbers shown in Table 1). The skilled person can easily isolate cDNAs of these nuclear reprogramming substances.

TABLE 1

| Gene Name | Mouse | Human |
| --- | --- | --- |
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |
| L-Myc | NM_008506 | NM_001033081 |

The mouse and human cDNA sequence data of the GLIS family members, the IRX family members, the PTX family members and DMRTB1 can be obtained with reference to the NCBI accession numbers shown in the following Table 2.

TABLE 2

| | Mouse | | Human | |
| --- | --- | --- | --- | --- |
| Gene name | cDNA | Protein | cDNA | Protein |
| IRX1 | NM_024337 | NP_077313 | NM_010573 | NP_034703 |
| IRX2 | NM_033267 | NP_150366 | NM_010574 | NP_034704 |
| IRX3 | NM_024336 | NP_077312 | NM_008393 | NP_032419 |
| IRX4 | NM_016358 | NP_057442 | NM_018885 | NP_061373 |
| IRX5 | NM_005853 | NP_005844 | NM_018826 | NP_061296 |
| IRX6 | NM_024335 | NP_077311 | NM_022428 | NP_071873 |

TABLE 2-continued

| Gene name | Mouse | | Human | |
| --- | --- | --- | --- | --- |
| | cDNA | Protein | cDNA | Protein |
| GLIS1 | NM_147193 | NP_671726 | NM_147221 | NP_671754 |
| GLIS2 | NM_032575 | NP_115964 | NM_031184 | NP_112461 |
| GLIS3 | NM_001042413 | NP_001035878 | NM_175459 | NP_780668 |
| PITX1 | NM_002653 | NP_002644 | NM_011097 | NP_035227 |
| PITX2 (isoform a) | NM_153427 | NP_700476 | NM_001042504 | NP_001035969 |
| PITX2 (isoform b) | NM_153426 | NP_700475 | NM_011098 | NP_035228 |
| PITX2 (isoform c) | NM_000325 | NP_000316 | NM_001042502 | NP_001035967 |
| PITX3 | NM_005029 | NP_005020 | NM_008852 | NP_032878 |
| DMRTB1 | NM_033067 | NP_149056 | XM_205469 | XP_205469 |

In addition, a native or artificial mutant protein which has sequence identity of 90% or more, preferably 95% or more, more preferably 98% or more, particularly preferably 99% or more to the amino acid sequence of the protein shown above and has a comparable ability to induce nuclear reprogramming as an substitute factor of Klf4 as compared to the corresponding wild-type protein, and also a nucleic acid encoding such a native or artificial mutant protein can be a nuclear reprogramming substance of the present invention usable in place of Klf4.

In the case where a protein factor of interest is used as it is as the nuclear reprogramming substance, the protein factor can be prepared by inserting the cDNA of the protein factor into an appropriate expression vector, introducing the expression vector into host cells, culturing the cells, and harvesting the protein factor as a recombinant protein from the culture. In the case where a nucleic acid encoding a protein factor of interest is used as the nuclear reprogramming substance, an expression vector for the protein factor is constructed by inserting the cDNA of the protein factor into a viral vector, a plasmid vector, an episomal vector or the like, and subjected to a nuclear reprogramming step.

In the case where the nuclear reprogramming substance is a protein factor, the introduction of the nuclear reprogramming substance into somatic cells can be performed by a method known per se for introducing proteins into cells. For example, the methods described in WO 2008/118820, WO 2010/098419, WO 2011/102531, WO 2011/004911, etc. may be used. The generation of iPS cells may be achieved by a procedure not involving genetic modification. Examples of such a method include a method using a protein transfection reagent, a method using a protein transduction domain (PTD)-fused protein or a cell-penetrating peptide (CPP)-fused protein, and the microinjection method. Examples of commercially available protein transfection reagents include cationic lipid-based reagents such as Bio-POTER Protein Delivery Reagent (Gene Therapy Systems), Pro-Ject™ Protein Transfection Reagent (PIERCE) and ProVectin (IMGENEX); lipid-based reagents such as Profect-1 (Targeting Systems); membrane-permeable peptide-based reagents such as Penetrain Peptide (Q biogene) and Chariot Kit (Active Motif); and GenomONE, an HVJ envelope (inactivated Sendai virus)-based reagent (Ishihara Sangyo). The introduction of the nuclear reprogramming substance can be performed according to the attached protocols of the commercially available protein transfection reagents.

Examples of practically used PTDs include the cell-permeable domains of *Drosophila* AntP, HIV TAT (Frankel, A. et al., Cell 55, 1189-93 (1988); Green, M. & Loewenstein, P. M. Cell 55, 1179-88 (1988)), penetratin (Derossi, D. et al., J. Biol. Chem. 269, 10444-50 (1994)), buforin II (Park C. B. et al., Proc. Natl. Acad. Sci. USA 97, 8245-50 (2000)), transportan (Pooga, M. et al., FASEB J. 12, 67-77 (1998)), MAP (model amphipathic peptide) (Oehlke, J. et al., Biochim. Biophys. Acta. 1414, 127-39 (1998)), K-FGF (Lin, Y. Z. et al., J. Biol. Chem. 270, 14255-14258 (1995)), Ku70 (Sawada, M. et al., Nature Cell Biol. 5, 352-7 (2003)), prion (Lundberg, P. et al., Biochem. Biophys. Res. Commun. 299, 85-90 (2002)), pVEC (Elmquist, A. et al., Exp. Cell Res. 269, 237-44 (2001)), Pep-1 (Morris, M. C. et al., Nature Biotechnol. 19, 1173-6 (2001)), Pep-7 (Gao, C. et al., Bioorg. Med. Chem. 10, 4057-65 (2002)), SynB1 (Rousselle, C. et al., Mol. Pharmacol. 57, 679-86 (2000)), HN-I (Hong, F. D. & Clayman, G. L. Cancer Res. 60, 6551-6 (2000)), HSV VP22 and other proteins. Examples of CPPs derived from PTDs include a polyarginine called 11R (Cell Stem Cell, 4: 381-384 (2009)) and a polyarginine called 9R (Cell Stem Cell, 4: 472-476 (2009)).

Prior to the introduction of the nuclear reprogramming substance, an expression vector for a PTD- or CPP-fused protein containing the cDNA of the nuclear reprogramming substance and a PTD- or CPP-encoding sequence is prepared, and the fusion protein is recombinantly expressed and then harvested. The introduction of the nuclear reprogramming substance can be performed in the same manner as described above in the protein transfection reagent-mediated method except that the protein transfection reagent is not used.

In the microinjection method, a glass needle with a tip end diameter of about 1 µm is loaded with a protein solution and inserted into a cell through the membrane to deliver the protein solution. This method enables reliable introduction of a protein of interest into cells.

In the case where a greater emphasis is placed on the efficiency of iPS cell generation, it is also preferable that the nuclear reprogramming substance is used in the form of a nucleic acid encoding a protein factor of interest, not in the form of a protein. The nucleic acid may be DNA, RNA or a DNA/RNA chimera, and the nucleic acid may be a double or single strand. Preferably, the nucleic acid is a double-stranded DNA, in particular cDNA.

The cDNA as the nuclear reprogramming substance is inserted in a suitable expression vector containing a promoter that can function in host somatic cells. Examples of the expression vector include viral vectors such as retroviral vectors, lentiviral vectors, adenoviral vectors, adeno-associated viral vectors, herpes virus vectors and sendai virus vectors; and animal cell expression plasmids (e.g., pA1-11, pXT1, pRc/CMV, pRc/RSV and pcDNAI/Neo).

The kind of the vector to be used is appropriately selected depending on the intended use of iPS cells to be generated. For example, adenoviral vectors, plasmid vectors, adeno-associated viral vectors, retroviral vectors, lentiviral vectors, sendai virus vectors, episomal vectors, etc. can be used.

Examples of the promoter used in the expression vector include an EF1α promoter, a CAG promoter, an SRα promoter, an SV40 promoter, an LTR promoter, a CMV (cytomegalovirus) promoter, an RSV (Rous sarcoma virus) promoter, MoMuLV (Moloney murine leukemia virus) LTR and an HSV-TK (herpes simplex virus thymidine kinase) promoter. Among them, preferred are an EF1α promoter, a CAG promoter, MoMuLV LTR, a CMV promoter, an SRα promoter, etc.

If desired, the expression vector may contain an enhancer, a poly A addition signal, a selection marker gene, an SV40 replication origin and/or the like in addition to the promoter. Examples of the selection marker gene include a dihydrofolate reductase gene, a neomycin resistance gene and a puromycin resistance gene.

The expression vector containing a nucleic acid as the nuclear reprogramming substance can be introduced into cells by a method which is known per se and appropriate for the kind of the vector. In an example where a viral vector is used as the expression vector, a plasmid containing the nucleic acid is introduced into appropriate packaging cells (e.g., Plat-E cells) or an appropriate complementing cell line (e.g., 293 cells), a viral vector produced in the culture supernatant is harvested, and cells are infected with the viral vector by a method appropriate for the kind of the viral vector. For example, a method using a retroviral vector as an expression vector is specifically described in WO 2007/69666; Cell, 126, 663-676 (2006); and Cell, 131, 861-872 (2007). A method using a lentiviral vector as an expression vector is specifically disclosed in Science, 318, 1917-1920 (2007).

In the case where a retroviral vector or a lentiviral vector is used as the expression vector, the transgene may be reactivated even after silenced. To avoid such a risk, for example, the Cre/loxP system is preferably used so that the nucleic acid encoding the nuclear reprogramming substance can be excised after no longer needed. Specifically, an expression vector containing two loxP sequences flanking the nucleic acid of interest is constructed and used for generation of iPS cells. After the generation of iPS cells, Cre recombinase is expressed using a plasmid vector or an adenoviral vector in the cells and allowed to act on the two loxP sites, and thereby the region between the loxP sequences can be excised. In addition, the enhancer-promoter sequences of LTR U3 region may upregulate neighboring host genes due to insertional mutagenesis. To avoid the regulation of the expression of endogenous genes by LTR which is neither flanked by the two loxP sequences nor anticipated to be removed from the genome, it is more preferable to use 3'-self-inactivating (SIN) LTR which can be obtained by deleting the sequence concerned or replacing the sequence concerned with an SV40 polyA sequence or the like. A method using the Cre-loxP system and SIN LTR is specifically disclosed in Chang et al., Stem Cells, 27: 1042-1049 (2009).

In the case where a non-viral plasmid vector is used as the expression vector, the vector can be introduced into cells by the lipofection method, the liposome method, the electroporation method, the calcium phosphate coprecipitation method, the DEAE dextran method, the microinjection method, the gene gun method or the like. A method using a plasmid as an expression vector is specifically described in, for example, Science, 322, 949-953 (2008) etc.

The procedure for gene transfer using a plasmid vector, an adenoviral vector or the like can be performed once or more times (for example, once to 10 times, or once to 5 times). For the transfer of two or more kinds of expression vectors per somatic cell, it is preferable that all these expression vectors are co-introduced into somatic cells. Also in this case, the procedure for gene transfer can be performed once or more times (for example, once to 10 times, or once to 5 times), and preferably repeated twice or more (for example, 3 or 4 times).

Another preferable non-integrating vector is an episomal vector, which is autonomously replicable as an extrachromosomal entity. A method using an episomal vector is specifically disclosed in Science, 324, 797-801 (2009).

In the case where the nuclear reprogramming substance is a low molecular weight compound, the introduction of the nuclear reprogramming substance into somatic cells can be performed as follows. The nuclear reprogramming substance is dissolved in an aqueous or non-aqueous solvent at an appropriate concentration, and the solution was added to a medium suitable for the culture of somatic cells isolated from a human or a mouse (for example, Minimum Essential Medium (MEM), Dulbecco's Modified Eagle's Medium (DMEM), RPMI1640 medium, 199 medium or F12 medium each supplemented with about 5 to 20% fetal bovine serum), at a concentration of the nuclear reprogramming substance that is sufficient for the induction of nuclear reprogramming in the somatic cells but causes no cytotoxicity. The somatic cells are cultured in the prepared medium for a given period. The concentration of the nuclear reprogramming substance varies with the kind of the nuclear reprogramming substance to be used, and is appropriately selected from the range of about 0.1 to 100 nM. The duration of the contact of the cells with the nuclear reprogramming substance is not particularly limited as long as the duration is sufficient to complete nuclear reprogramming of the cells. In general, the cells are incubated in a medium containing the nuclear reprogramming substance until positive colonies emerge.

The contact of the somatic cells with, in addition to the nuclear reprogramming substance, a substance for enhancing the efficiency of iPS cell generation (hereinafter referred to as an iPS cell generation enhancer) is expected to enhance the efficiency of iPS cell generation. Examples of the iPS cell generation enhancer include histone deacetylase (HDAC) inhibitors [e.g., low molecular inhibitors such as valproic acid (VPA) (Nat. Biotechnol., 26 (7): 795-797 (2008)), trichostatin A, sodium butyrate, MC 1293 and M344; and nucleic acids for downregulation of gene expression such as siRNAs and shRNAs against HDAC (e.g., HDAC1 siRNA Smartpool (registered trademark) (Millipore), HuSH 29 mer shRNA Constructs against HDAC1 (OriGene), etc.)]; DNA methyltransferase inhibitors (e.g., 5'-azacytidine) (Nat. Biotechnol., 26 (7): 795-797 (2008)); G9a histone methyltransferase inhibitors [e.g., low molecular inhibitors such as BIX-01294 (Cell Stem Cell, 2: 525-528 (2008)); and nucleic acids for downregulation of gene expression such as siRNAs and shRNAs against G9a (e.g., G9a siRNA (human) (Santa Cruz Biotechnology) etc.)]; L-channel calcium agonists (e.g., Bayk8644) (Cell Stem Cell, 3, 568-574 (2008)); p53 inhibitors (e.g., siRNAs and shRNAs against p53) (Cell Stem Cell, 3, 475-479 (2008)); UTF1 (Cell Stem Cell, 3, 475-479 (2008)); Wnt signaling (e.g., soluble Wnt3a) (Cell Stem Cell, 3, 132-135 (2008)); and 2i/LIF (2i is an inhibitor of mitogen-activated protein kinase signaling and glycogen synthase kinase-3 (PloS Biology, 6 (10), 2237-2247 (2008)). However, these are non-limiting examples. The above-mentioned nucleic acids for downregulation of gene expression may be in the form of an expression vector containing a DNA encoding siRNA or shRNA.

Some of the components as the nuclear reprogramming substance in the present invention, for example, SV40 large T etc. can also be included in the "iPS cell generation enhancer" as used herein from the viewpoint that they are not essential but auxiliary factors for nuclear reprogramming of somatic cells. Under the current circumstances, the mechanism of nuclear reprogramming is not clearly understood, and auxiliary factors, i.e., factors other than essential factors for nuclear reprogramming may be conveniently categorized as the nuclear reprogramming substance or as the iPS cell generation enhancer. That is, the nuclear reprogramming process of somatic cells can be regarded as a comprehensive phenomenon triggered by the contact of somatic cells with the nuclear reprogramming substance and the iPS cell generation enhancer, and therefore there is no need for those skilled in the art to clearly distinguish between the two.

The procedure for the contact of the somatic cells with the iPS cell generation enhancer varies with the type of the iPS cell generation enhancer. The iPS cell generation enhancer can be (a) a protein factor, (b) a nucleic acid encoding the protein factor or (c) a low molecular weight compound. The procedure for the contact is the same as described regarding the contact of the somatic cells with the corresponding type of the nuclear reprogramming substance.

The contact of the somatic cells with the iPS cell generation enhancer may coincide with, or precede or follow the contact of the somatic cells with the nuclear reprogramming substance as long as the efficiency of iPS cell generation from the somatic cells is significantly increased in the presence of the enhancer as compared with that in the absence of the enhancer. In one embodiment, for example, in the case where the nuclear reprogramming substance is a nucleic acid encoding a protein factor of interest and the iPS cell generation enhancer is a chemical inhibitor, gene-transfer treatment and subsequent culture for a certain period can be followed by addition of the iPS cell generation enhancer to a medium. This is because a certain period of time is required after the gene-transfer treatment to allow the overexpression of the protein factor, while the chemical inhibitor can quickly act on the cells. In another embodiment, for example, in the case where both the nuclear reprogramming substance and the iPS cell generation enhancer are used in the form of a viral vector or a plasmid vector, both of them may be co-introduced into the cells.

Before the nuclear reprogramming step, somatic cells isolated from a mammal may be precultured in a culture medium which is known per se and appropriate for the type of the cells. Examples of the medium include Minimum Essential Medium (MEM), Dulbecco's Modified Eagle's Medium (DMEM), RPMI1640 medium, 199 medium and F12 medium each supplemented with about 5 to 20% fetal bovine serum. These are non-limiting examples. In the case where a transfection reagent such as a cationic liposome is used for the contact of the somatic cells with the nuclear reprogramming substance and the iPS cell generation enhancer, it may be preferable that the medium is replaced with a serum-free medium in advance for the prevention of decline in transfection efficiency. After the contact with the nuclear reprogramming substance (and the iPS cell generation enhancer), the cells are cultured, for example, under the conditions suitable for ES cell culture. In the case of mouse cells, the cells are cultured in a medium prepared by adding leukemia inhibitory factor (LIF) as a differentiation inhibitor to a usual medium. In the case of human cells, the medium desirably contains a basic fibroblast growth factor (bFGF) and/or a stem cell factor (SCF) instead of LIF.

The cells are usually co-cultured with feeder cells, for example, mouse embryonic fibroblasts (MEFs) whose division has been arrested by radiation or antibiotic treatment, but can be cultured under feeder-free conditions. As the MEFs, STO cells etc. are usually often used, and SNL cells (McMahon, A. P. & Bradley, A. Cell 62, 1073-1085 (1990)) etc. are often used for the generation of iPS cells. The co-culture with feeder cells may start before the contact with the nuclear reprogramming substance, at the same time of the contact, or after the contact (for example, 1 to 10 days later).

The selection of candidate iPS cell colonies can be done by a method using drug resistance and reporter activity as indicators or by a method based on visual observation of cell morphology. In one example of the former method, recombinant cells prepared by targeting the locus of a gene highly expressed specifically inpluripotent cells (e.g., Fbx15, Nanog, Oct3/4, etc., preferably, Nanog or Oct3/4) with a drug resistance gene and/or a reporter gene are used, and a colony which is resistant to the drug and/or positive for the reporter activity is selected (see Takahashi et al., Cell, 131, 861-872 (2007), for example). Examples of such recombinant cells include MEFs derived from a knock-in mouse having the βgeo gene (encoding a fusion protein of β-galactosidase and neomycin phosphotransferase) inserted in the Fbx15 locus (Takahashi & Yamanaka, Cell, 126, 663-676 (2006)); and MEFs derived from a transgenic mouse created by insertion of the green fluorescent protein (GFP) gene and the puromycin resistance gene into the Nanog locus (Okita et al., Nature, 448, 313-317 (2007)). Examples of the method for selecting a candidate colony by visual observation of cell morphology include the method described in Takahashi et al., Cell, 131, 861-872 (2007). In the case where three factors Oct3/4, Klf4 and Sox2 are used as the nuclear reprogramming substance, most of the resulting colonies are formed of high-quality iPS cells comparable to ES cells, albeit a smaller number of the established clones. In this case, efficient establishment of iPS cells can be achieved without the use of reporter cells.

The identification of the cells in the selected colony as iPS cells can be made from the Nanog (or Oct3/4) reporter positive (puromycin resistant, GFP positive, etc.) reaction and from ES cell-like colony formation determined by visual observation. For more accurate identification, the expression of ES cell-specific genes may be analyzed, and the potency of teratoma formation etc. may be tested by transplanting the cells in the selected colony to a mouse. The method for confirming that the iPS cells are maintained in an undifferentiated state is not particularly limited, and may be a method based on the detection of the mRNAs of conventionally known undifferentiation markers (e.g., endogenous alkaline phosphatase, Oct3/4, Sox2, Nanog, Eras, Esg1, etc.) etc. as indicators. Alternatively, immunochemical techniques (e.g., immunostaining, western blot, ELISA, etc.) may be used to confirm the expression of these indicators. The method for confirming the pluripotency of the obtained iPS cells is not particularly limited, and for example, teratoma formation is examined by transplanting the iPS cells to immunodeficient animal models (SCID mice etc.). In this examination, the pluripotency of the obtained iPS cells can be confirmed by the formation of cell clumps (tissues) derived from the three germ layers in teratoma.

The iPS cells used in the present invention may be in the form of an embryoid body or an aggregate. The method for aggregate formation is not particularly limited, and for example, the method described in Sasaki et al.: Tissue Eng Part A, 16 (8): 2497-2504, 2010 etc. can be used.

Conventional human ES cells derived from a blastocyst-stage embryo are very different from mouse ES cells in biological (morphological, molecular and functional) properties. Mouse pluripotent stem cells can exist in two functionally distinct states, i.e., LIF-dependent ES cells and bFGF-dependent epiblast stem cells (EpiSCs). The pluripotent state of human ES cells has been shown to be similar to that of mouse EpiSCs rather than that of mouse ES cells according to molecular analyses. Recently, human ES or iPS cells in a mouse ES cell-like pluripotent state (also called naive human ES or iPS cells) have been established by inducing ectopic expression of Oct3/4, Sox2, Klf4, c-Myc and Nanog in the presence of LIF (see Cell Stem Cell, 6: 535-546, 2010), or by inducing ectopic expression of Oct3/4, Sox2 and Klf4 in the presence of LIF in combination with a GSKP inhibitor and an ERK1/2 pathway inhibitor (see Proc. Natl. Acad. Sci. USA, article first published online; doi/10.1073/pnas. 1004584107). Such naive human ES or iPS cells are in a more immature, pluripotent state as compared to conventional human ES or iPS cells, and therefore are preferable as the source material used in the present invention.

As for the inactivated cell construct used in the bone regeneration agent of the present invention, its measured FT-IR (KBr) spectrum preferably at least has a peak for a phosphate at around 1000±200 cm$^{-1}$, a peak for amide II at around 1550±100 cm$^{-1}$ and a peak for amide I at around 1650±100 cm$^{-1}$. More preferably, in addition to these peaks, a peak for a carbonate at around 850±100 cm$^{-1}$ is present in the FT-IR (KBr) spectrum. The FT-IR (KBr) spectrum can be measured by a known method.

The inactivated cell construct used in the bone regeneration agent of the present invention at least contains a mineral and an extracellular matrix. The bone regeneration agent of the present invention may comprise a known bone regenerative material or a known bone substitute material in addition to the inactivated cell construct. Examples of the known bone regenerative material or the known bone substitute material include hydroxyapatite, β-TCP (β-tricalcium phosphate) and collagen sponge.

The inactivated cell construct may contain a substance other than a mineral or an extracellular matrix unless the effects of the present invention are hindered. The inactivated cell construct can be obtained by inactivation of a cell aggregate at least containing a mineral and an extracellular matrix.

The cell aggregate can be obtained by inducing differentiation of stem cells into mineral-producing cells.

The mineral is not particularly limited, and the examples include calcium-based substances. The calcium-based substance is not particularly limited, and the examples include calcium phosphate-based substances, calcium carbonate-based substances, calcium lactate and calcium gluconate. The calcium phosphate-based substance is not particularly limited, and the examples include one kind or a mixture of two kinds or more selected from hydroxyapatite, carbonate apatite, fluorapatite, chlorapatite, β-TCP, α-TCP, calcium metaphosphate, tetracalcium phosphate, calcium hydrogen phosphate, calcium dihydrogen phosphate, calcium pyrophosphate, calcium carbonate and calcium sulfate, and salts or solvates of the foregoing compounds. Preferred are j-TCP and hydroxyapatite. Examples of the calcium carbonate-based substance include calcium carbonate and calcium hydrogen carbonate, and calcium carbonate is preferred. As long as the calcium-based substance is mainly composed of any of the above-listed compounds, the calcium-based substance may contain other compounds etc. as appropriate.

The extracellular matrix is not particularly limited, and the examples include naturally-occurring polymers such as osteonectin, thrombospondin, vitronectin, fibrin, osteopontin, bone sialoprotein, osteocalcin, collagen, phosphophoryn, heparan sulfate, heparin, laminin, fibronectin, alginic acid, proteoglycan (hyaluronan, fibromodulin, etc.), chitin and growth factors (BMP, FGF-2 (fibroblast growth factor 2 (basic FGF)), TGFβ (transforming growth factor-β), PDGF (platelet-derived growth factor) and VEGF (vascular endothelial growth factor), etc.). Preferred are collagen and growth factors. The extracellular matrix may be composed of a single substance or two or more substances selected from these polymers. In a preferable example, the extracellular matrix is mainly composed of a collagen protein. The term "mainly composed" means that the component concerned accounts for 50% or more of all components. The collagen content of the extracellular matrix mainly composed of a collagen protein should be 50% or more, but no other particular limitations are imposed. The collagen content is preferably 70% or more, and more preferably 80% or more. The collagen is preferably type I collagen, type II collagen, type III collagen, type IV collagen, type V collagen, type X collagen or the like, for example.

The inactivated cell construct of the present invention is not particularly limited, but is preferably an inactivated cell construct containing calcium phosphate as crystalline hydroxyapatite and type I collagen in large quantity.

The bone regeneration agent of the present invention may further comprise an osteoblastic differentiation-inducing factor or other factors unless the effects of the present invention are hindered. Examples of the osteoblastic differentiation-inducing factor include compounds such as ascorbic acid, ascorbic acid 2-phosphate, β-glycerophosphoric acid, dexamethasone, hydrocortisone hemisuccinate, statin, isoflavone derivatives, the 3-benzothiepine derivative TAK-778 ((2R,4S)-(-)-N-[4-(diethoxyphosphorylmethyl)phenyl]-1,2,4,5-tetrahydro-4-methyl-7,8-methylenedioxy-5-oxo-3-benzothiepin-2-carboxamide), compound A described in paragraph [0023] of Japanese Patent No. 2992677, the helioxanthin derivative TH (4-(4-methoxyphenyl)pyrido[40,30:4,5]thieno[2,3-b]pyridine-2-carboxamide), phenamil (3,5-diamino-6-chloro-N-[imino(phenylamino)methyl]pyrazine-2-carboxamide), harmine and its analogs, acerogenin and its analogs (for example, acerogenin B, which is represented by the following formula:

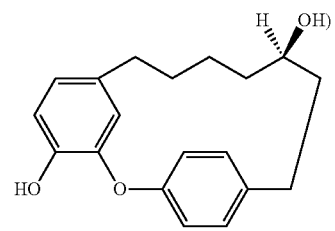

and resveratrol; proteins associated with bone formation; and differentiation inducers described in WO 2006/123699, JP-A 2004/083504, etc. Preferred are one or more kinds selected from the group consisting of dexamethasone, β-glycerophosphoric acid and ascorbic acid 2-phosphate.

The protein associated with bone formation is not particularly limited as long as it is associated with the growth, proliferation or formation of osteocytes and/or osteoblasts, or the promotion of these phenomena. The examples include bone morphogenetic proteins (BMPs), osteogenin, platelet-rich plasma (PRP), enamel matrix derivative (trade name: Emdogain (registered trademark)), platelet-derived growth factors 1.5 (PDGFs) and fibroblast growth factors (FGFs) (preferably FGF-2). The BMP is not particularly limited, and may be any of the isoforms such as BMP-1, BMP-2, BMP-3, BMP-4, BMP-5, BMP-6, BMP-7, BMP-8, BMP-8B and BMP-9. Preferred are BMP-2, BMP-4, BMP-5, BMP-7 and BMP-9. These differentiation inducing factors may be used alone or in a combination of two or more kinds thereof. In the case where a specific set of differentiation inducing factors (for example, one or more kinds selected from the group consisting of dexamethasone, β-glycerophosphoric acid and ascorbic acid 2-phosphate) is used, another differentiation inducing factor may or may not be contained in the set.

The calcium content per inactivated cell construct may vary with the type of cells (iPS cells, ES cells, mesenchymal stem cells, etc.), the species of origin of cells (a human, a mouse), the type of cell clone, etc., and is not particularly limited. For example, in the case of using mouse iPS cells, the calcium content of all inactivated cell constructs formed in a 25-cm$^2$ culture flask used in Example 1 is preferably 10 mg or more/flask because such an amount is highly effective for bone regeneration. The method for measuring the calcium content is as described later in Examples.

The surface area of the inactivated cell construct may vary with the type of cells (iPS cells, ES cells, mesenchymal stem cells, etc.), the species of origin of cells (a human, a mouse), the type of cell clone, etc., and is not particularly limited.

For example, in the case of using mouse iPS cells, the area measured on a phase-contrast microscopic image of the inactivated cell construct using the image-analysis software ImageJ (National Institutes of Health, U.S.) is preferably 300000 m- or more considering the bone regenerative effect and easy handling.

The maximum diameter of the inactivated cell construct may vary with the type of cells (iPS cells, ES cells, mesenchymal stem cells, etc.), the species of origin of cells (a human, a mouse), the type of cell clone, etc., and is not particularly limited. For example, in the case of using mouse iPS cells, the maximum diameter of the inactivated cell construct is preferably 0.1 to 5.0 mm, more preferably 0.5 to 2.0 mm considering the bone regeneration effect and easy handling.

The method for producing the bone regeneration agent of the present invention will be described hereinafter.

An embodiment of the method for producing the bone regeneration agent of the present invention is a method comprising the steps of:
(1) inducing differentiation of stem cells into mineral-producing cells in agitated culture under the condition of 0.01 to 1.00 Hz to give a cell aggregate at least containing a mineral and an extracellular matrix, and
(2) inactivating the cell aggregate obtained in the preceding step.

The stem cells may be precultured prior to step (1). The method for the preculture is not particularly limited, and can be a conventionally known one. For example, the stem cells are cultured in an adherent culture system in a culture vessel. Alternatively, the stem cells are cultured in an adherent culture system in a culture vessel until grown to 70 to 80% confluency, transferred to a low-attachment culture plate, and cultured in a suspension culture system at 37° C.

Step (1) involves inducing differentiation of the stem cells into mineral-producing cells in agitated culture. The agitated culture in step (1) is usually performed under the condition of 0.01 to 1.00 Hz. For formation of larger-sized cell aggregates, the agitated culture is performed under the condition of preferably 0.05 to 0.80 Hz, more preferably 0.10 to 0.70 Hz, and particularly preferably 0.15 to 0.45 Hz. It is not preferable that the agitated culture is performed under the condition of less than 0.01 Hz, because the size of the resulting cell aggregate is not large enough for the purpose of the present invention. It is also not preferable that the agitated culture is performed under the condition of more than 1.00 Hz, because the size of the resulting cell aggregate is not large enough for the purpose of the present invention.

For the induction of differentiation in step (1), stem cells are cultured in a medium suitable for differentiation into specialized cells of interest. The medium used for induced differentiation can be a known one. The examples include such serum-free media as Minimum Essential Medium (MEM), Dulbecco's Modified Eagle's Medium (DMEM), RPMI1640 medium, 199 medium, F12 medium and a mixed medium thereof. Also included are media prepared by supplementing any of the above-listed basal media with an appropriate concentration of a well-known conventional medium additive (e.g., S-Clone medium (e.g., SF-03; Sanko Junyaku)). Examples of the medium additive include growth factors such as a fibroblast growth factor (FGF), an endothelial cell growth factor (EGF) and a platelet-derived growth factor (PDGF); antibiotics such as penicillin, streptomycin, amphotericin B, gentamicin and kanamycin; carbon sources such as glucose, galactose, fructose and sucrose; trace minerals such as magnesium, iron, zinc, calcium, potassium, sodium, copper, selenium, cobalt, tin, molybdenum, nickel and silicon; anti-oxidants such as 2-mercaptoethanol, catalase, superoxide dismutase and N-acetylcysteine; and others such as adenosine 5'-monophosphate, corticosterone, ethanolamine, insulin, reduced glutathione, lipoic acid, hypoxanthine, phenol red, progesterone, putrescine, pyruvic acid, thymidine, triiodothyronine, serum albumin, transferrin and lactoferrin. The medium for induced differentiation used in the present invention is not limited to the media described above. The medium for induced differentiation may further contain an osteoblastic differentiation inducer and/or the like.

Specific examples of the medium for induced differentiation include a DMEM supplemented with 100 nM dexamethasone, 10 mM β-glycerophosphoric acid, 0.25 mM ascorbate and 10% fetal bovine serum (FBS) (Pittenger M F et al., Science 284: 143, 1999); and an α-MEM supplemented with 15% fetal bovine serum (FBS), 0.1 μM dexamethasone, 10 mM β-glycerophosphoric acid, 50 μM ascorbic acid 2-phosphate, 100 units/mL penicillin, 100 μg/mL streptomycin and 250 ng/mL amphotericin B (Egusa H, Schweizer F E, Wang C C, Matsuka Y, Nishimura I, Neuronal differentiation of bone marrow-derived stromal stem cells involves suppression of discordant phenotypes through gene silencing. J. Biol. Chem. 2005 Jun. 24; 280 (25): 23691-7).

The method for the agitated culture in the present invention is not particularly limited, and for example, the agitated culture can be performed on a seesaw bioreactor as shown in FIG. 1. The agitation angle in the agitated culture is not particularly limited, but is preferably 250 or less, more preferably 20 or less, still more preferably 15° or less against the horizontal direction. The agitation amplitude in the agitated culture is not particularly limited, and for example, may be about 0.10 to 2.0 cm. In FIG. 1, the inclination angle is 106, r (the radius of a 25-cm² flask) is 2.5 cm, and the amplitude is 0.43 cm.

The cell concentration at the start of the culture in step (1) is not particularly limited. For example, in the case where a 25-cm² culture flask is used, the cell concentration is preferably about $1\times10^4$ to $1\times10^8$ cells/flask, and more preferably about $1\times10^6$ to $7\times10^6$ cells/flask.

The culture temperature in step (1) is not particularly limited, but is usually 33 to 40° C., preferably 35 to 37° C. In addition, step (1) is preferably performed in an atmosphere of 5% $CO_2$.

The period of the agitated culture is not particularly limited. For formation of cell aggregates large enough in size for use as a bone substitute material, the culture period is preferably 5 days or more, more preferably 10 days or more, and still more preferably 20 days or more. The upper limit of the culture period is not particularly specified, and may be about 100 days, which is long enough to allow the formation of cell aggregates large enough in size.

In step (1), it is optional and preferable that the medium further contains an osteoblastic differentiation-inducing factor as appropriate. The differentiation inducer is as described above.

After the agitated culture, the cell aggregates are suspended in a solution such as sodium citrate buffer and phosphate buffered saline (PBS), and then harvested.

Step (2) is a step of inactivating the cell aggregates obtained in step (1). This step produces the above-mentioned inactivated cell constructs. The inactivation method in this step is not particularly limited, and the examples include lyophilization, heat treatment, high pressure treatment, acid or alkali solution treatment, autoclave sterilization, radiation sterilization and gas sterilization. The conditions of the lyophilization are not particularly limited, and known lyophilization methods can be employed. Optionally, preliminary freezing may precede the lyophilization. The temperature of the preliminary freezing is not particularly limited, but is preferably about −12 to −20° C., for example. The lyophilization temperature is not particularly limited, but is preferably about −100 to −5° C. The lyophilization pressure is not particularly limited, but is preferably 600 Pa or less, more preferably 50 Pa or less, for example. In a specific example, lyophilization is performed under the conditions where the temperature is fixed at −10° C. and the pressure is gradually reduced to 5 to 20 Pa from the level at the start of the lyophilization.

The bone regeneration agent of the present invention is not particularly limited as long as it comprises the inactivated cell construct obtained in the preceding step. The inactivated cell construct may be packed by wetting with physiological saline.

In another embodiment of the method for producing the bone regeneration agent of the present invention, a method comprising the steps of:
(1') inducing differentiation of stem cells genetically engineered to overexpress a protein associated with bone formation into mineral-producing cells in agitated or static culture, to give a cell aggregate at least containing a mineral and an extracellular matrix, and
(2) inactivating the cell aggregate obtained in the preceding step.

In step (1'), stem cells genetically engineered to overexpress a protein associated with bone formation are induced to differentiate into mineral-producing cells by culturing the stem cells in agitated or static culture, and thereby a cell aggregate at least containing a mineral and an extracellular matrix is obtained.

Figure 2:
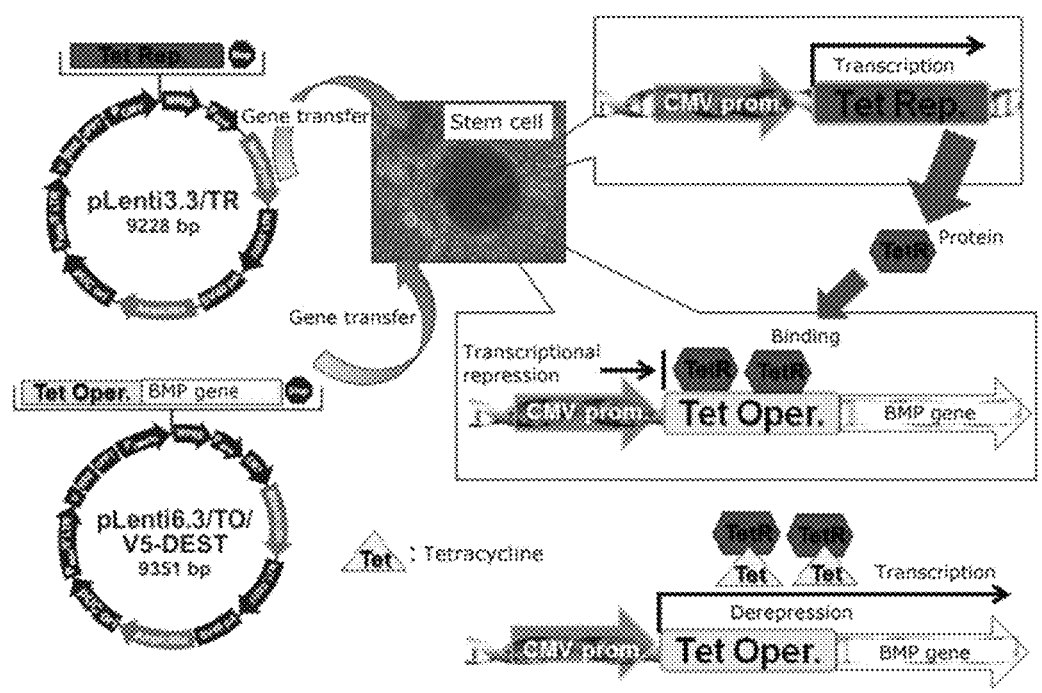
FIG. 2 shows an embodiment of the production method of the bone regeneration agent of the present invention.

The method for genetically engineering stem cells to overexpress a protein associated with bone formation is not particularly limited, and can be a known one. For example, a tetracycline-dependent gene expression regulatory system as shown in FIG. 2 may be used.

The protein associated with bone formation is not particularly limited, and the examples include growth factors including the above-mentioned bone morphogenetic proteins (BMPs). Examples of growth factors other BMPs include FGF-2, TGFβ, PDGF, VEGF and type I collagen. Preferable BMPs are BMP2 and BMP4. These proteins may be used alone or in a combination of two or more.

The method for genetically engineering stem cells to overexpress a protein associated with bone formation may comprise DNA cloning, plasmid construction, gene transfer to a host, transformant culture and doxycycline (tetracycline derivative) addition (in the case of using a tetracycline-dependent gene expression regulatory system). These procedures can be performed according to methods known to those skilled in the art, the methods described in the following documents (Molecular Cloning, T. Maniatis et al., CSH Laboratory (1983), DNA Cloning, D M. Glover, IRL PRESS (1985), J. Sambrook, E. F. Fritsch & T. Maniatis (Ed.), Molecular cloning, a laboratory manual (3rd edition), Cold Spring Harbor Press, Cold Spring Harbor, N.Y. (2001); F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd.), etc.

When the above-described method for overexpression of a protein associated with bone formation is employed, a favorable bone regeneration agent can be produced even in static culture, not necessarily in agitated culture. Also in the method for overexpression of a protein associated with bone formation, agitated culture may be employed. The agitated culture is as described above.

The method for the static culture is not particularly limited. The culture temperature is usually 33 to 40° C. and preferably 35 to 37° C. In addition, step (1') is preferably performed in an atmosphere of 5% $CO_2$.

Another embodiment of the present invention is a method for tissue regeneration comprising a step of administering, to a human or a non-human mammal in need of tissue regeneration, the bone regeneration agent of the present invention described above, that is, a bone regeneration agent comprising an inactivated cell construct derived from stem cells as a source material, the inactivated cell construct at least containing a mineral and an extracellular matrix.

Yet another embodiment of the present invention is a method for tissue regeneration comprising a step of administering, to a human or a non-human mammal in need of tissue regeneration, a bone regeneration agent obtained by a method comprising the steps of:
(1) inducing differentiation of stem cells into mineral-producing cells in agitated culture under the condition of 0.01 to 1.00 Hz to give a cell aggregate at least containing a mineral and an extracellular matrix, or
(1') inducing differentiation of stem cells genetically engineered to overexpress a protein associated with bone formation into mineral-producing cells in agitated or static culture, to give a cell aggregate at least containing a mineral and an extracellular matrix, and
(2) inactivating the cell aggregate obtained in the preceding step.

Steps (1), (1') and (2) are as described above. The bone regeneration agent to be administered may be composed of only the inactivated cell construct obtained in step (2). Alternatively, as described above, a cofactor such as growth factors and bone morphogenetic proteins may also be contained in the bone regeneration agent unless the effects of the present invention are hindered.

The bone regeneration agent of the present invention may be administered to any subject and the examples of the subject include humans and non-human mammals (mice, rats, pigs, cows, sheep, monkeys, rabbits, cats, dogs, etc.).

In particular, the bone regeneration agent of the present invention can be administered to a human or a non-human mammal in need of regeneration of tissues such as bone, more particularly a human or a non-human mammal with bone injury or bone defect, and the administration method can be, for example, implantation into the site of the bone injury or the bone defect. Examples of the bone injury or the bone defect include fracture, intra-articular injury, bone tumor excision, for example, bone defect associated with surgery such as arthrodesis, bone defect caused by alveolar ridge (alveolar bone) resorption, and alveolar bone defect after tooth extraction (tooth extraction socket).

The dose of the bone regeneration agent of the present invention is not particularly limited as long as it is a pharmaceutically effective amount and does not hinder the effects of the present invention. The dose varies with the subject, the body weight, the disease and the condition of the subject, etc.

The present invention includes embodiments in which the above-described constitutions are combined differently within the technical scope of the present invention as long as these embodiments produce the effects of the present invention.

EXAMPLES

Hereinafter, the present invention will be illustrated in more detail by examples, but the present invention is not limited thereto. Many variations can be made by those having ordinary knowledge in the art within the scope of the technical idea of the present invention.

Example 1

1. Mouse iPS Cells

An iPS cell line established by introducing the genes of Oct3/4, Sox2 and Klf4 to adult mouse gingival fibroblasts using a retroviral vector (PLoS ONE, 5 (9): e12743, 2010) was used in the following experiment. The iPS cells were maintained and cultured on SNLP76.7-4 feeder cells (mitomycin-C treated: $2.1 \times 10^5$ cells/well) seeded on a 6-well tissue culture plate (coated with 0.1% gelatin) in an ES medium [a DMEM medium (Nacalai Tesque) supplemented by 15% fetal bovine serum (Invitrogen), 2 mM L-glutamine (Invitrogen), $1 \times 10^{-4}$ M non-essential amino acid (Invitrogen), $1 \times 10^{-4}$ M 2-mercaptoethanol (Invitrogen), 50 U penicillin and 50 µg/mL streptomycin (Invitrogen)].

2. Generation of Embryoid Bodies from iPS Cells

After grown to 80% confluence, the iPS cells on the 6-well tissue culture plate were treated with 0.25% trypsin/1 mM EDTA (550 µL, room temperature, 1 to 3 minutes) and entirely collected. The collected cells were transferred to a 10-cm low-attachment culture dish containing an ES medium (10 mL) and cultured in a floating culture system. During 2-day floating culture, the iPS cells formed embryoid bodies.

The embryoid bodies formed from iPS cells were collected by centrifugation (300 rpm, 1 minute), and seeded on a low-attachment culture dish containing an ES medium (10 mL) supplemented with 1 µM retinoic acid (all-trans retinoic acid: Sigma). During 2-day floating culture, the iPS cells in the embryoid bodies were differentiated into mesodermal cells (Kawaguchi J: Methods Mol Biol 330: 135-148).

3. Directed Differentiation of iPS Cell-Derived Embryoid Bodies into Osteoblasts After the four days of floating culture in total, the iPS cell-derived embryoid bodies were collected by centrifugation (300 rpm, 1 minute) and suspended in an osteoblastic differentiation medium [an α-MEM medium (Nacalai Tesque) supplemented with 10% fetal bovine serum (Invitrogen), 0.1 µM dexamethasone (Sigma), 10 mM β-glycerophosphoric acid (Sigma), 50 µg/mL ascorbic acid 2-phosphate (Sigma), 100 units/mL penicillin, 100 µg/mL streptomycin and 250 ng/mL amphotericin B (Invitrogen)]. For the measurement of the cell concentration in the cell suspension, a portion of the suspension was treated with 0.25% trypsin/1 mM EDTA (37° C., 10 minutes) and subjected to cell counting with a cell counter (trade name: Z1D Coulter Counter, Beckman Coulter). The remaining cell suspension was seeded on a suspension culture flask (Iwaki: 1103-025: non-treated surface, with bent cap, 25-cm$^2$ usable surface area) at a cell density of $4 \times 10^6$ cells in 10 mL of the osteoblastic differentiation medium.

The culture flask was placed onto a seesaw shaker (Wave-SI: Taitec) and the iPS cell-derived embryoid bodies were cultured with agitation (inclination angle: 10°, frequency: 0.33 Hz (1 stroke/3 seconds), amplitude: 0.43 cm). During the culture, the medium was freshly replaced every 2 to 3 days and the cell aggregates were transferred to a new culture flask at each medium replacement.

4. Inactivation of Cell Aggregates Derived from iPS Cells

Figure 3:
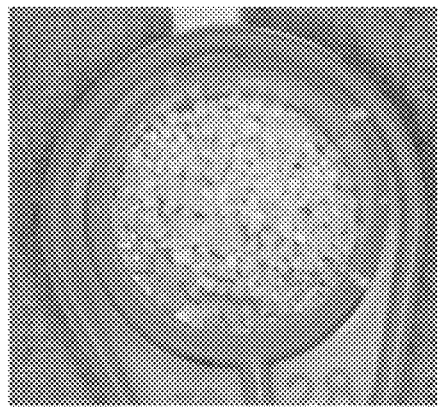
FIG. 3 show an image of the bone regeneration agent of Example 1.

The whole cell suspension was transferred to a 15-mL centrifugation tube at 30 days after the start of the agitated culture. After the completion of spontaneous precipitation of the cell aggregates derived from IPS cells in the cell suspension, the culture supernatant was removed by aspiration. The cell aggregates were washed with PBS twice and immersed in a 10 mL of sodium citrate buffer (20 mM, pH 6.0, plus 100 mg/mL sucrose) or PBS at 4° C. overnight. On the following day, the cell aggregates were taken out from the cell suspension, transferred to a 6-cm cell culture dish, and preliminarily frozen in a freezer at −80° C. overnight. After that, the dish was placed in a freeze dryer (trade name: JFD-320 Freeze Drying Device, JEOL), and the pressure was gradually reduced to 6 to 20 Pa at a fixed temperature of −10° C. overnight for inactivation of the cell aggregates. Thus, inactivated cell constructs were obtained as a bone regeneration agent. The dish containing the bone regeneration agent was covered with a lid, hermetically sealed with a piece of seal, and stored in a moisture-proof storage (glass desiccator). An image of the obtained bone regeneration agent is represented in FIG. 3.

Examples 2 to 4

A bone regeneration agent was obtained in the same manner as described in Example 1, except that the period of the agitated culture was 10, 20 or 40 days.

Experimental Example 1

Figure 4:
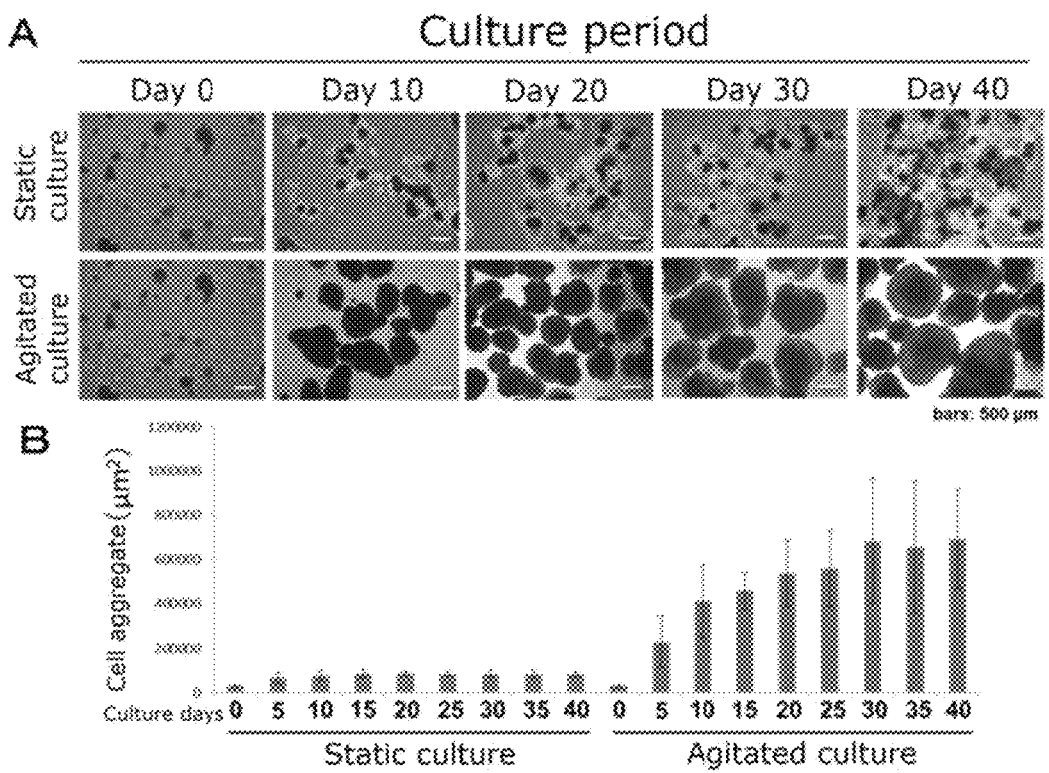
FIG. 4 shows the results of Test Example 1. A shows the results of the observation of cell aggregates after the indicated culture periods. B shows the surface areas ($\mu m^2$) of cell aggregates after the indicated culture periods.

Differentiation culture was performed in the same manner as described in Examples 1 to 4, and the resulting cell aggregates were photographed under phase-contrast microscopy at 5-day intervals for 40 days. For a control group (control), the same procedure as in Examples 1 to 4 was performed except that static culture was performed for induced differentiation instead of agitated culture, and the resulting cell aggregates were photographed as described above. A partial section of each photographed image is shown in FIG. 4A. The total area of ten randomly selected cell aggregates on each photographed image was measured with the image-analysis software ImageJ (National Institutes of Health, U.S.) and the mean and the standard deviation were calculated. The results are shown in FIG. 4B.

The area per cell aggregate derived from iPS cells in the case of agitated culture increased over time and reached the plateau after 30 days. The area after 30 days of agitated culture was about 23 times larger than that at the start of the culture. On the other hand, the area per cell aggregate derived from iPS cells in the case of static culture was not significantly increased after 40 days. As with the static culture, agitated culture under the condition of 1.0 Hz resulted in no increase in the size of the cell aggregate derived from iPS cells.

These results demonstrate that the agitated culture in this experiment increases the size of the osteoblast aggregate derived from iPS cells. The area per cell aggregate measured after 30 days of agitated culture was 382,878 to 1,269,456 $\mu m^2$ (mean: 680,986 $\mu m^2$), which corresponds to about 0.7 to 1.2 mm (mean: about 0.9 mm) in diameter. In consideration that the diameters of commercial bone substitute materials are in the range of 0.5 to 2 mm, the size of the cell aggregate obtained by the agitated culture method used in this experiment is suitable as a bone regeneration agent or a bone substitute material.

Experimental Example 2

Figure 5:
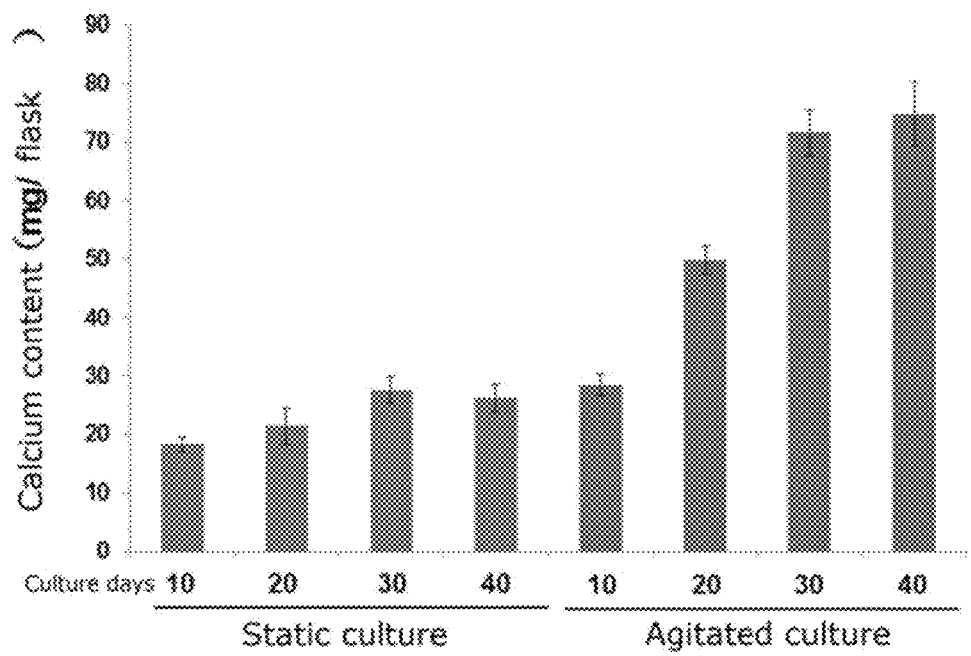
FIG. 5 shows the calcium contents (mg/flask) of cell aggregates in Test Example 2.

Differentiation culture was performed in the same manner as described in Examples 1 to 4, and the calcium content of the cell aggregates derived from iPS cells at 10, 20, 30 or 40 days after the start of the differentiation culture was measured. For a control group (control), the same procedure as in Examples 1 to 4 was performed except that static culture was performed for induced differentiation instead of agitated culture, and the calcium content of the resulting cell aggregates derived from iPS cells was measured. The calcium content was measured as follows. The cell aggregates derived from iPS cells in a flask were entirely harvested, washed with PBS twice and immersed in 10 mL of 0.5 M acetic acid at room temperature overnight. The sample was homogenized with a homogenizer (homogenization pestle) and the homogenate was centrifuged (2, 300 g, 10 minutes). The supernatant was harvested, and the calcium concentration of the supernatant was measured by the MXB method (calcium E-Test Wako, Wako Pure Chemical Industries, Ltd.) in terms of absorbance (OD) at 595 nm. The experiment was independently repeated three times. In each experiment, the absorbance measurement was conducted in quintuplicate, and the mean and the standard deviation were calculated. The results are shown in FIG. 5.

Whether agitated culture or static culture was performed, the calcium content of the cell aggregates derived from iPS cells significantly increased over time and reached the plateau after 30 days (P<0.01: ANOVA, Tukey-Kramer multiple comparison test). In each of the measurement time points (10 to 40 days), the calcium content of the cell aggregates derived from iPS cells in the case of agitated culture was significantly larger than that in the case of static culture (P<0.001: ANOVA, Tukey-Kramer multiple comparison test). The calcium content of the cell aggregates derived from iPS cells at 40 days after the start of agitated culture was about 3 times larger than that in the case of static culture.

These results demonstrate that agitated culture resulted in an increase in calcium production in the osteoblast aggregates derived from iPS cells.

Experimental Example 3

Figure 6:
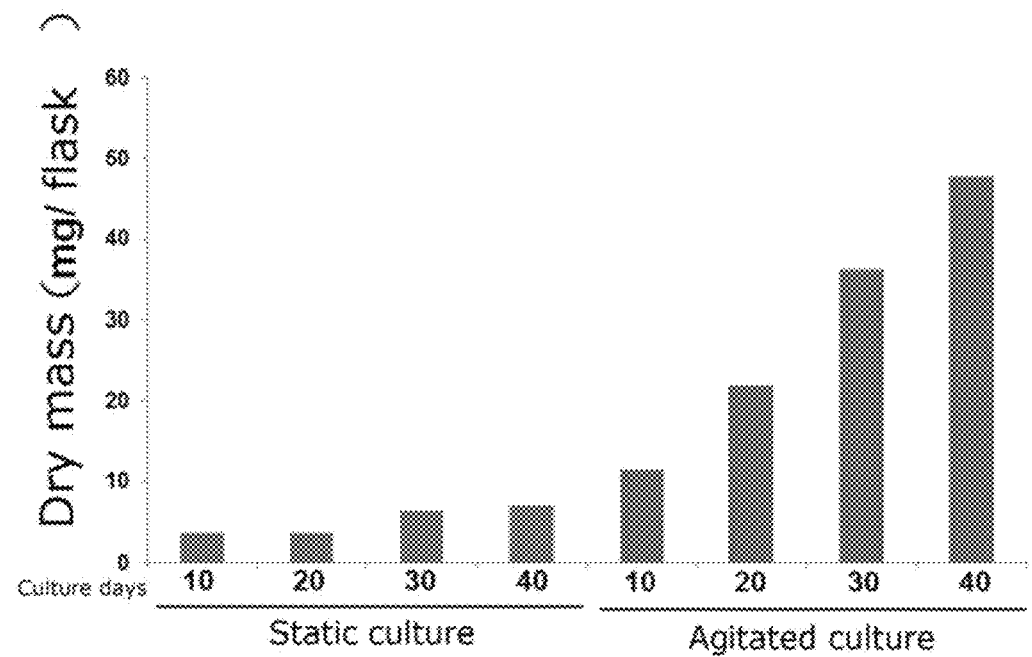
FIG. 6 shows the dry weights (mg/flask) of cell aggregates in Test Example 3.

Differentiation culture was performed in the same manner as described in Examples 1 to 4, and the cell aggregates derived from iPS cells in a culture flask were entirely harvested at 10, 20, 30 or 40 days after the start of the differentiation culture and fixed with a 10% neutral buffered formalin solution (Wako Pure Chemical Industries, Ltd.) at 4° C. overnight. After the fixation, the cell sample was washed (immersed for 5 minutes) with distilled water 3 times and gradually dehydrated with increasing concentrations of ethanol from 30% to 100%. After that, the cell sample was left stand in a dryer at 37° C. for 12 hours and subjected to mass measurement. For a control group (control), the same procedure as in Examples 1 to 4 was performed except that static culture was performed for induced differentiation instead of agitated culture. The results are shown in FIG. 6.

Whether agitated culture or static culture was performed, the mass of the cell aggregates derived from iPS cells increased over time. In each of the measurement time points (10 to 40 days), the mass of the cell aggregates derived from iPS cells in the case of agitated culture was significantly larger than that in the case of static culture. These results demonstrate that agitated culture resulted in an increase in the mass of the osteoblast aggregates derived from iPS cells.

Experimental Example 4

Figure 7:
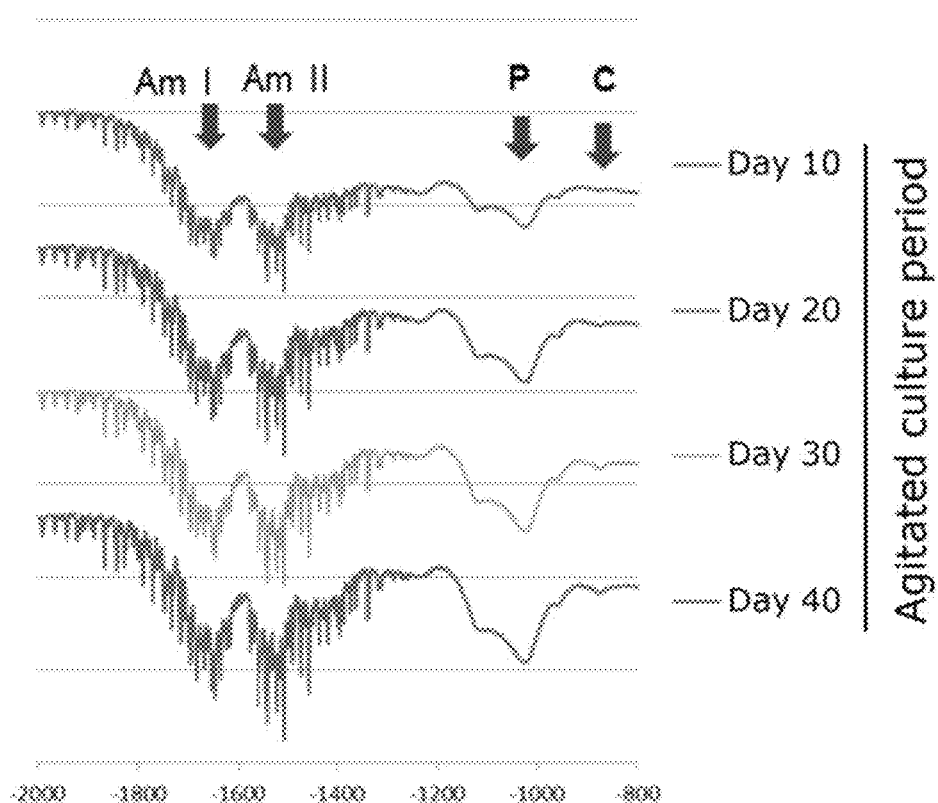
FIG. 7 shows the results of FT-IR (KBr) spectroscopy.

Differentiation culture was performed in the same manner as described in Examples 1 to 4, and the cell aggregates derived from iPS cells in a culture flask were entirely harvested at 10, 20, 30 or 40 days after the start of the differentiation culture and fixed with a 10% neutral buffered formalin solution (Wako Pure Chemical Industries, Ltd.) at 4° C. overnight. After the fixation, the cell sample was washed (immersed for 5 minutes) with distilled water 3 times and gradually dehydrated with increasing concentrations of ethanol from 30% to 100%. After that, the cell sample was left stand in a dryer at 37° C. for 12 hours. The dried cell sample was mixed with potassium bromide (KBr) so that the concentration of the dried cell sample would be 2 wt %, and subjected to Fourier transform infrared (FT-IR) spectroscopy. For FT-IR spectroscopy, each sample was scanned 50 times over a range of 2,000 to 800 $cm^{-1}$ at a resolution of 1 cm$^{-1}$ using FTIR-8300 (Shimadzu Corporation) and the infrared absorption spectrum was obtained. The results are shown in FIG. 7.

The results of the FT-IR spectroscopy demonstrate that the longer the culture period of the iPS cells, the higher peaks indicating the presence of the phosphate group (P) associated with hydroxyapatite and the presence of the carboxyl group (C) associated with carbonate apatite in the matrix rich in amino acids (AmI, AmII). In particular, the cell aggregates derived from iPS cells after 30 to 40 days of culture showed an FT-IR absorption spectrum pattern specific to bone tissue (see Table 1 and FIG. 1 in Boskey A. et al., Biomaterials, 28 (15): 2465-78 (2007); and FIG. 6 in Cambra-Moo O. et al., J. Struct. Biol., 178 (3): 338-49 (2012)).

These results demonstrate that the cell aggregates derived from iPS cells after 30 days or more of agitated culture in the osteoblastic differentiation medium have a composition similar to that of bone tissue.

Test Example 1

Figure 8:
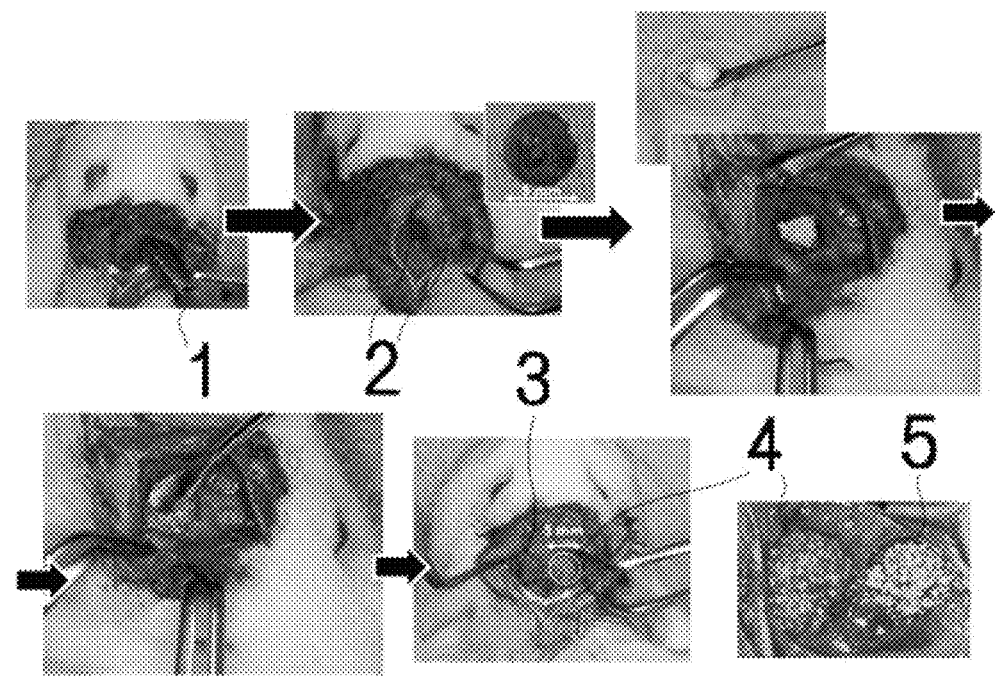
FIG. 8 shows the test method in Test Example 1.

An animal experiment on bone defect replacement surgery was conducted as shown in FIG. 8 using the bone regeneration agent obtained in Examples.

The specific procedure is as follows. A 5-mm-diameter dental trephine bur 1 was used to drill holes in the skull at the right and left sides in 10-week-old male Sprague-Dawley rats, and 5-mm-diameter calvarial bone defects 2 were created. Eight milligrams of the bone regeneration agent of Example 1, which was produced from the cell aggregates derived from iPS cells after 30 days of agitated culture, was wet with several drops of physiological saline, was injected into the site of one of the bone defects. The injection site was covered with periosteum and the scalp was closed by suture. For Comparative Examples, collagen sponge (Terudermis, Collagen Monolayer Type: Olympus Terumo Biomaterials Corp. (Comparative Example 1)), OSferion (trade name, diameter: 0.5 to 1.5 mm: Olympus Terumo Biomaterials Corp. (Comparative Example 2)), or nothing (no injection (Comparative Example 3)) was injected.

Figure 11:
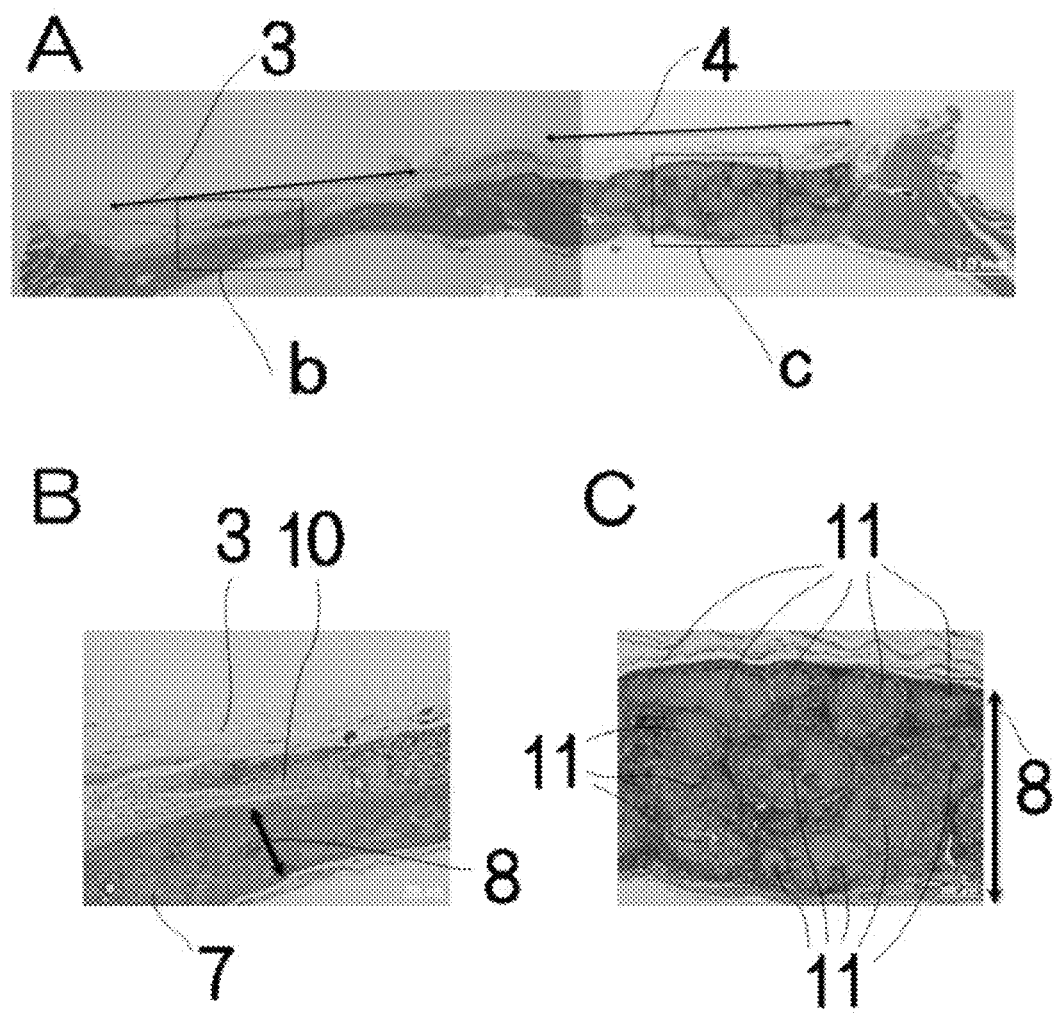
FIG. 11 shows the results of HE staining of the skull resected 5 weeks after the bone replacement surgery in Test Example 1.
Figure 12:
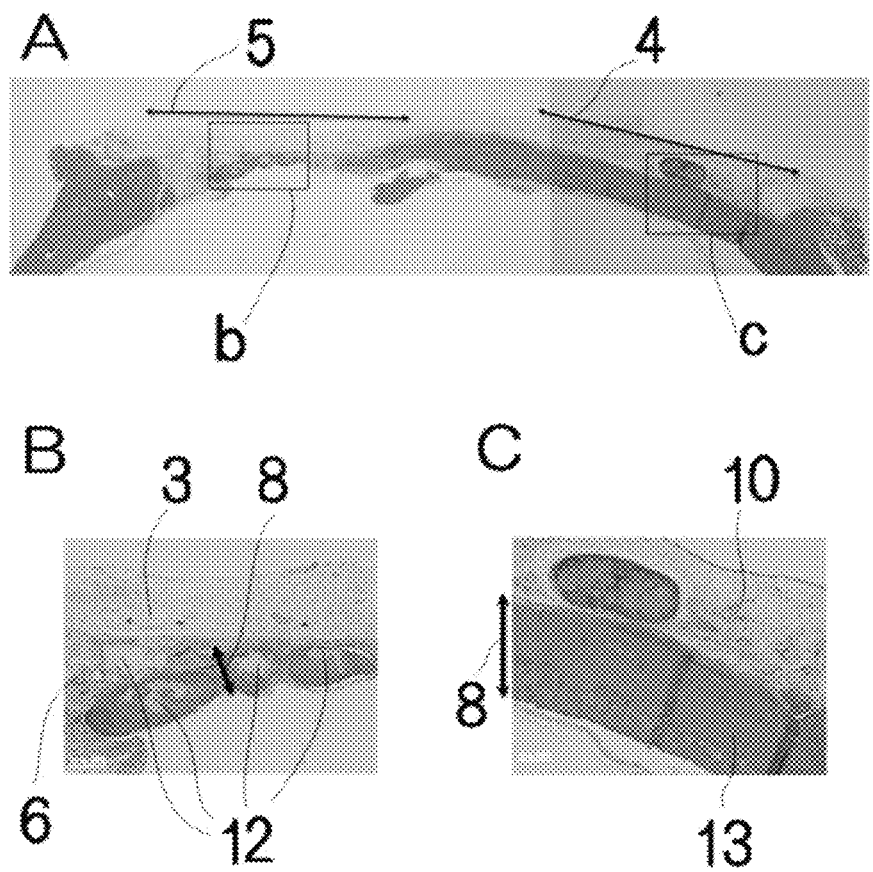
FIG. 12 shows the results of HE staining of the skull resected 8 weeks after the bone replacement surgery in Test Example 1.
Figure 13:
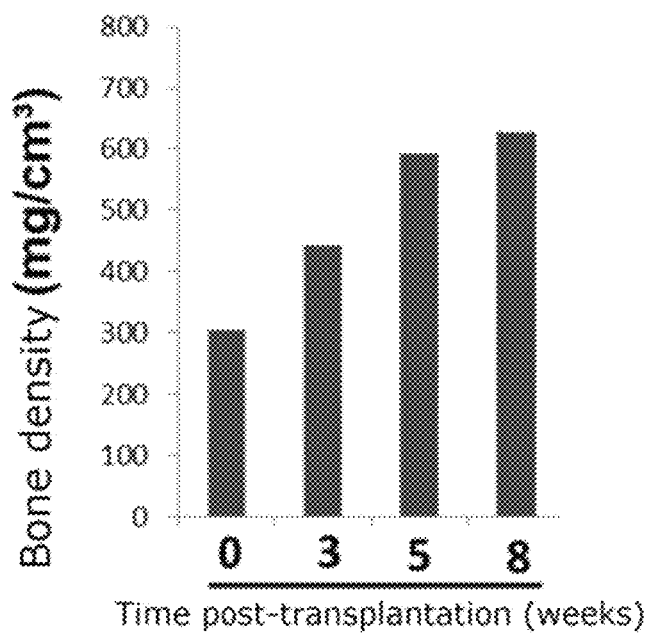
FIG. 13 shows the results of the micro X-ray CT analysis in Test Example 1.

The skull was resected after 3, 5 or 8 weeks of breeding and photographed with a micro CT scanner (R_mCT2, 3D X-ray micro CT for experimental animals: Rigaku Corporation), and the bone density was measured with a bone-structural analysis software (TRI/3D-BON: Ratoc System Engineering Co., Ltd.). Moreover, the skull was immersed in a 10% neutral buffered formalin solution for fixation, demineralized, and embedded with paraffin. The paraffin-embedded specimen was sliced into 3-μm-thick sections. The sections were subjected to hematoxylin and eosin (H&E) staining and subsequent histological observation. The results are shown in FIGS. 9 to 12. The results of micro CT analysis are shown in FIG. 13.

Figure 9:
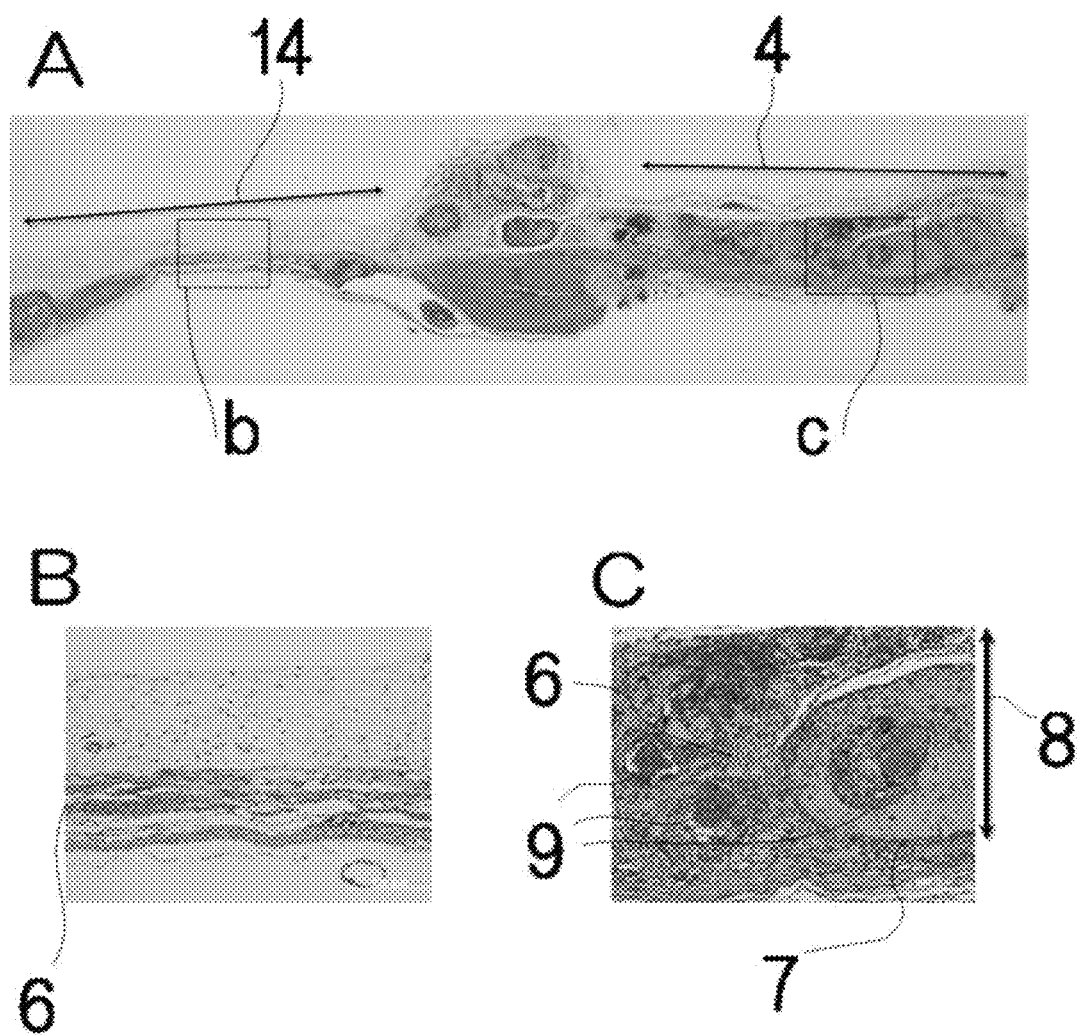
FIG. 9 shows the results of HE staining of the skull resected 3 weeks after the bone replacement surgery in Test Example 1.
Figure 10:
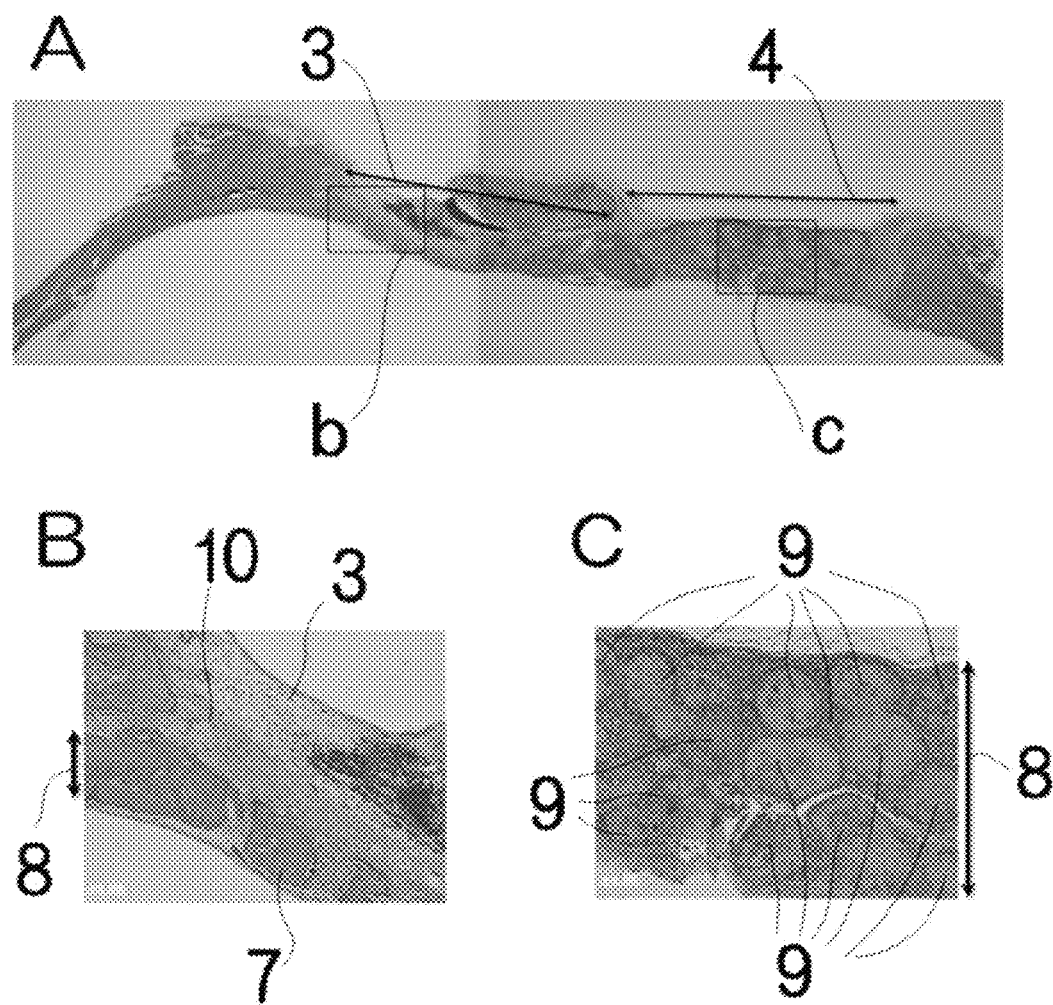
FIG. 10 shows the results of HE staining of the skull resected 3 weeks after the bone replacement surgery in Test Example 1.

FIG. 9 shows the results of HE staining of the skull resected 3 weeks after the bone replacement surgery. FIG. 10 shows the results of HE staining of the skull resected 3 weeks after the bone replacement surgery. FIG. 11 shows the results of HE staining of the skull resected 5 weeks after the bone replacement surgery. FIG. 12 shows the results of HE staining of the skull resected 8 weeks after the bone replacement surgery.

As shown in FIG. 9, the bone regeneration agent of the present invention formed a new bone with a certain amount of thickness at 3 weeks after the bone replacement surgery unlike the no-injection site, and vertical bone regeneration was achieved. As shown in FIG. 10, the bone regeneration agent of the present invention formed a new bone twice or more thicker than that in the collagen sponge-injected site at 3 weeks after the bone replacement surgery. The injection of the bone regeneration agent of the present invention caused no neoplastic transformation at any time point after the surgery.

As shown in FIG. 11, the site filled with the bone regeneration agent of the present invention was appropriately replaced with natural bone without the reduction in vertical thickness in comparison with the collagen sponge-injected site at 5 weeks after the bone replacement surgery, and favorable bone tissue regeneration was achieved.

As shown in FIG. 12, the site filled with the bone regeneration agent of the present invention was fully replaced with new bone without the reduction in vertical thickness at 8 weeks after the bone replacement surgery, and mature cortical bone was formed. Meanwhile, in the case where OSferion was injected, this bone substitute material still remained in the injection site without replacement with new bone at 8 weeks after the transplant surgery, and satisfactory results were not obtained in terms of the thickness of regenerated bone or the formation of cortical bone.

As shown in FIG. 13, the bone density in the bone defect site filled with the bone substitute material of the present invention was increased over time after the injection. This shows that the bone substitute material of the present invention injected into the bone defect site was certainly replaced with new bone.

As is clear from the above descriptions, the bone regeneration agent of the present invention was confirmed to enable vertical bone regeneration without neoplastic transformation and thick bone restoration.

INDUSTRIAL APPLICABILITY

The bone regeneration agent of the present invention is not only useful as artificial bones and bone substitute materials, fracture treatment materials, joint treatment materials, etc. in the medical field, but also useful as bone substitute materials for periodontal disease treatment, inhibitors of alveolar ridge resorption in tooth extraction sockets, alveolar regeneration agents for implant treatment, etc. in the dentistry field.

REFERENCE SIGNS LIST

1 Trephine bur
2 Bone defect
3 Collagen sponge
4 Bone regeneration agent (iPS cell preparation)
5 OSferion
6 Immature bone
7 New bone
8 Thick bone restoration
9 Bone regeneration agent (iPS cell preparation) surrounded by new bone
10 Fibrous tissue
11 Bone regeneration agent (iPS cell preparation) replaced with new bone
12 OSferion being replaced with new bone
13 Mature cortical bone
14 No injection

The invention claimed is:

1. A method for producing a bone regeneration agent, the bone regeneration agent comprising a cell aggregate comprising an inactivated cell construct, a mineral and an extracellular matrix, wherein the inactivated cell construct is derived from stem cells as a source material, wherein the stem cell is one or more types selected from the group consisting of an embryonic stem (ES) cell, an embryonic germ (EG) cell and an induced pluripotent stem (iPS) cell, the method comprising the steps of:

(a) inducing differentiation of the stem cells into mineral-producing cells in culture, wherein the culture is agitated at a frequency of 0.01 to 1.00 Hz to give the cell aggregate at least containing the mineral-producing cells, the mineral and the extracellular matrix, and (b) inactivating the cell aggregate obtained in (a) wherein the cell aggregate is inactivated by one or more methods selected from the group consisting of lyophilization, freezing, heat treatment, high pressure treatment, acid solution treatment, alkali solution treatment, autoclave sterilization, radiation sterilization and gas sterilization.

2. The method according to claim 1, wherein the inactivation is performed by lyophilization.

3. The method according to claim 1, wherein the extracellular matrix is mainly composed of a collagen protein.

4. The method according to claim 1, wherein the agitated culture in step (a) is performed in the presence of an osteoblastic differentiation-inducing factor.

5. The method according to claim 4, wherein the osteoblastic differentiation-inducing factor is one or more kinds selected from the group consisting of dexamethasone, β-glycerophosphoric acid and ascorbic acid 2-phosphate.

6. The method according to claim 1, wherein the period of the agitated culture is 30 days or more.

* * * * *